United States Patent
Park et al.

(10) Patent No.: US 9,498,519 B2
(45) Date of Patent: Nov. 22, 2016

(54) AMYLOID-BETA CLEARANCE

(75) Inventors: Woo Jin Park, Gwangju (KR);
Hye-eun Han, Gwangju (KR)

(73) Assignee: GWANGJU INSTITUTE OF SCIENCE AND TECHNOLOGY, Buk-Gu, Gwangju (KR)

( * ) Notice: Subject to any disclaimer, the term of this patent is extended or adjusted under 35 U.S.C. 154(b) by 372 days.

(21) Appl. No.: 13/701,332

(22) PCT Filed: Jul. 23, 2010

(86) PCT No.: PCT/KR2010/004854
§ 371 (c)(1),
(2), (4) Date: Jan. 10, 2013

(87) PCT Pub. No.: WO2012/011621
PCT Pub. Date: Jan. 26, 2012

(65) Prior Publication Data
US 2013/0108613 A1    May 2, 2013

(51) Int. Cl.
A61K 38/48 (2006.01)
A61K 48/00 (2006.01)
C12N 9/50 (2006.01)
A61K 38/46 (2006.01)
A61K 38/43 (2006.01)

(52) U.S. Cl.
CPC ......... *A61K 38/4873* (2013.01); *A61K 48/005* (2013.01); *C12N 9/506* (2013.01); *C12Y 304/22044* (2013.01); *C12N 2740/15043* (2013.01); *C12N 2770/34022* (2013.01); *C12N 2770/34033* (2013.01); *C12N 2770/34071* (2013.01)

(58) Field of Classification Search
CPC ............. C12N 2770/34033; C12Y 304/22044
USPC ....................................................... 424/94.65
See application file for complete search history.

(56) References Cited

U.S. PATENT DOCUMENTS

| 7,494,786 B2 | 2/2009 | Doudna et al. |
| 2005/0003547 A1* | 1/2005 | Spencer et al. ............ 435/456 |
| 2005/0175581 A1* | 8/2005 | Haupts et al. ............ 424/85.1 |
| 2010/0209422 A1 | 8/2010 | Ravetch et al. |

FOREIGN PATENT DOCUMENTS

KR    10-2010-0074297 A    7/2010

OTHER PUBLICATIONS

Koike et al., "Watercress" in Vegetable Diseases, 2006, Manson Publishing, pp. 416-417.*
Koike et al., "Watercress", Vegetable Diseases, 2007, Manson Publishing, pp. 416-418.*
Godyn et al., "Therapeutic strategies for Alzheimer's disease in clinical trials", 2016, Pharmacological Reports, 68, 127-138.*

(Continued)

*Primary Examiner* — Sharmila G. Landau
*Assistant Examiner* — Sheridan Macauley
(74) *Attorney, Agent, or Firm* — Nath, Goldberg & Meyer; Joshua B. Goldberg; Tanya E. Harkins

(57) ABSTRACT

The present invention relates to a pharmaceutical composition for preventing or treating an amyloid β-caused disease, which comprises as an active ingredient a NIa (nuclear inclusion a) protease or a gene carrier containing a nucleotide sequence encoding the NIa protease. The pharmaceutical composition of this invention is very effective to treat a variety of diseases or disorders, inter alia, Alzheimer's disease.

9 Claims, 19 Drawing Sheets

(56) References Cited

OTHER PUBLICATIONS

Sinha, S. et al. "Cellular mechanisms of β-amyloid production and secretion", Proc. Natl. Acad. Sci., vol. 96, pp. 11049-11053, (Sep. 1999).

Shaked, G. M., et al., "Interactions between the amyloid precursor protein C-terminal domain and G proteins mediate calcium dysregulation and amyloid β toxicity in Alzheimer's disease", FEBS Journal 276, pp. 2736-2751, (2009).

Rorrer, K. et al., " Autocatalytic activity of the tobacco etch virus NIa proteinase in viral and foreign protein sequences", Journal of General Virology, 73, pp. 775-783, (1992).

"Nuclear Inclusion Protein a, Partial (Turnip Mosaic Virus)", Accession AAA89116, http://www.ncbi.nlm.hih.gov/protein/aaa89116.1, Feb. 27, 1996.

Kim, et al., "Charachterization of NIa Protease from Turnip Mosaic Potyvirus Exhibiting a Low-temperature Optimum Catalytic Activity", Virology 221, pp. 245-249, 1996.

* cited by examiner

Non injection

Lenti-NIa

SEQUENCE LISTING

```
<160> NUMBER OF SEQ ID NOS: 3

<210> SEQ ID NO 1
<211> LENGTH: 243
<212> TYPE: PRT
<213> ORGANISM: Potyvirus Turnip mosaic virus

<400> SEQUENCE: 1

Ser Asn Ser Met Phe Arg Gly Leu Arg Asp Tyr Asn Pro Ile Ser Asn
1               5                   10                  15

Asn Ile Cys His Leu Thr Asn Val Ser Asp Gly Ala Ser Asn Ser Leu
            20                  25                  30

Tyr Gly Val Gly Phe Gly Pro Leu Ile Leu Thr Asn Arg His Leu Phe
        35                  40                  45

Glu Arg Asn Asn Gly Glu Leu Val Ile Lys Ser Arg His Gly Glu Phe
    50                  55                  60

Val Ile Lys Asn Thr Thr Gln Leu His Leu Leu Pro Ile Pro Asp Arg
65                  70                  75                  80

Asp Leu Leu Leu Ile Arg Leu Pro Lys Asp Ile Pro Pro Phe Pro Gln
                85                  90                  95

Lys Leu Gly Phe Arg Gln Pro Glu Lys Gly Glu Arg Ile Cys Met Val
            100                 105                 110

Gly Ser Asn Phe Gln Thr Lys Ser Ile Thr Ser Val Val Ser Glu Thr
        115                 120                 125

Ser Thr Ile Met Pro Val Glu Asn Ser Gln Phe Trp Lys His Trp Ile
    130                 135                 140

Ser Thr Lys Asp Gly Gln Cys Gly Ser Pro Met Val Ser Thr Lys Asp
145                 150                 155                 160

Gly Lys Ile Leu Gly Leu His Ser Leu Ala Asn Phe Gln Asn Ser Ile
                165                 170                 175

Asn Tyr Phe Ala Ala Phe Pro Asp Asp Phe Ala Glu Lys Tyr Leu His
            180                 185                 190

Thr Ile Glu Ala His Glu Trp Val Lys His Trp Lys Tyr Asn Thr Ser
        195                 200                 205

Ala Ile Ser Trp Gly Ser Leu Asn Ile Gln Ala Ser Gln Pro Ser Gly
    210                 215                 220

Leu Phe Lys Val Ser Lys Leu Ile Ser Asp Leu Asp Ser Thr Ala Val
225                 230                 235                 240

Tyr Ala Gln
```

-continued

```
<210> SEQ ID NO 2
<211> LENGTH: 732
<212> TYPE: DNA
<213> ORGANISM: Potyvirus Turnip mosaic virus

<400> SEQUENCE: 2
gagagtaact ccatgttcag agggttgcgt gattacaacc caatatcaaa caacatttgt     60
catctcacaa atgtttcaga tggagcatca aactcgttat atggagtcgg tttcggacca    120
ctcatattaa cgaaccgaca cctctttgag cggaataacg gtgaactcgt aataaaatca    180
cgacatggtg agttcgtgat taaaaacaca actcagctac atttgctacc gattccagac    240
agagatctcc tgctaatccg gttaccaaag gacatcccac cctttccaca gaaattgggt    300
ttcaggcaac ctgagaaggg tgagcgaatc tgcatggtgg ggtccaactt ccaaactaag    360
agcataacga gtgtagtctc tgagactagc acaataatgc cagtggaaaa cagtcagttt    420
tggaaacact ggattagcac gaaagacggc caatgcggaa gtccaatggt gagcacgaaa    480
gacgggaaaa tacttggact acacagccta gcaaacttcc agaattccat taattacttt    540
gctgctttcc cagatgattt tgccgagaag tatctccata ccattgaagc acacgagtgg    600
gtcaagcatt ggaaatataa tactagtgcc atcagctggg gctctttgaa tatacaagca    660
tcgcaaccgt caggtttgtt caaagtaagc aaactaatct cagacctcga cagcacggca    720
gtctacgcac aa                                                        732

<210> SEQ ID NO 3
<211> LENGTH: 42
<212> TYPE: PRT
<213> ORGANISM: Homo sapiens

<400> SEQUENCE: 3

Asp Ala Glu Phe Arg His Asp Ser Gly Tyr Glu Val His His Gln Lys
  1               5                   10                  15

Leu Val Phe Phe Ala Glu Asp Val Gly Ser Asn Lys Gly Ala Ile Ile
             20                  25                  30

Gly Leu Met Val Gly Gly Val Val Ile Ala
         35                  40
```

AMYLOID-BETA CLEARANCE

This is a National Phase Application filed under 35 U.S.C. 371 as a national stage of PCT/KR2010/004854, filed Jul. 23, 2010, the content of which is hereby incorporated by reference in its entirety.

BACKGROUND OF THE INVENTION

Field of the Invention

The present invention relates to a pharmaceutical composition and a method for preventing or treating various amyloid β-caused diseases.

"The Sequence Listing submitted in text format (.txt) on Jan. 10, 2013, named "PP100055US RSequenceListing.txt", (created on Jan. 3, 2013, 4KB), is incorporated herein by reference."

Description of the Related Art

Alzheimer's disease (AD) is a progressive neurodegenerative disorders which affects approximately twenty four million people worldwide, and it is the most common form of dementia among older people. AD is characterized by progressive memory impairment and cognitive dysfunction. A distinct hallmark of AD is the deposition of amyloid plaques which are mainly composed of amyloid β (Aβ) of 40, 42, and 43 amino acids in length. Aβ is produced by the sequential cleavage of the amyloid β precursor protein (APP) by β- and γ-secretases[1,2]. Aβ can exist in different forms such as monomers, oligomers (dimer, trimer, and tetramer), proto-fibrils, and fibrils, and these different conformational states are related to its toxicity. Oligomeric Aβ was shown to be approximately 10- and 40-fold more cytotoxic than fibrillar and monomeric Aβ, respectively[3]. A recent report also found that dimeric Aβ are 3-fold more toxic than monomeric Aβ, and that trimeric and tetrameric Aβ are upto 13-fold more toxic[4].

Although Aβ unquestionably plays a causative role in AD, the underlying mechanisms by which it contributes to the development of this disease are still controversial. It is widely accepted that Aβ exerts its pathological activity extracellularly. In pathological AD brains, Aβ is secreted into the extracellular space forming amyloid plaques[5]. When added into the culture media, Aβ can induce cell death in vitro in a variety of cell types[3,4,6].

However, accumulating evidence suggests that intracellular Aβ activity is also critical for the development of AD. Several authors have reported the intracellular localization of Aβ in the brain tissues of post-mortem AD patients and in transgenic AD mice[1,7,8]. A closer examination with electron microscopy and immunocytochemistry revealed that Aβ is present in diverse subcellular organelles in neuronally differentiated P19 cells, including early endosomes, trans-Golgi network, rough endoplasmic reticulum, outer mitochondrial membrane, and nuclear envelope[9]. In a triple transgenic AD mouse model, early cognitive impairments correlated with the accumulation of intracellular Aβ in the hippocampus and amygdala, without the apparent deposition of amyloid plaques or neurifibrillary tangles[10].

Intracellular Aβ was also shown to induce p53-dependent neuronal cell death[11,12] through the impairment of mitochondrial function[13]. The intra-hippocampal injection of an antibody directed against Aβ reduced not only extracellular Aβ deposits, but also intracellular Aβ accumulation. Upon dissipation of this antibody, the re-appearance of the extracellular deposits was preceded by the accumulation of intracellular Aβ. These observations suggest that a dynamic exchange between intracellular and extracellular Aβ exists, and that intracellular Aβ serves as a source of extracellular amyloid deposits, implying a role for intracellular Aβ in the pathogenesis of AD[14,15].

Since the accumulation of Aβ is considered to be the most critical single event in the pathogenesis of AD, a catabolic elimination of Aβ from the brain would be a valuable therapeutic strategy. Several proteases, including neprilysin (NEP), insulin degrading enzyme, endothelin-converting enzyme, and uPA/tPA-plasmine, have been identified for their ability to degrade Aβ[16], with NEP being the best-characterized one. The pharmacological inhibition or genetic ablation of NEP in mice has been shown to result in an increased Aβ deposition, accompanied by deficits in synaptic plasticity and an impairment in hippocampus-dependent memory[17,18], while the viral or transgene-mediated overexpression of NEP reduced Aβ deposition and its associated cytopathology[19,20]. However, it was recently shown that NEP overexpression did not reduce the oligomeric Aβ levels or improve deficits in learning and memory. These results appear to suggest that the NEP-dependent degradation of Aβ affected plaques more efficiently than oligomeric Aβ[21].

Throughout this application, various patents and publications are referenced, and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive endeavors to develop proteolytic therapeutics for amyloid β-caused diseases, inter alia, Alzheimer's disease. As a result, we have discovered that the nuclear inclusion a (NIa) protease of Turnip mosaic virus (TuMV) cleaves monomeric and oligomeric amyloid β (Aβ) in an effective and specific manner and significantly prevents the Aβ-induced cell death in neuronal culture cells and the Aβ-related pathology in transgenic AD (Alzheimer's disease) mice. NIa might therefore provide a novel strategy for the clearance of toxic oligomeric Aβ from the brain of AD patients.

Accordingly, it is an object of this invention to provide a pharmaceutical composition for preventing or treating an amyloid β-caused disease.

It is another object of this invention to provide a method for preventing or treating an amyloid β-caused disease.

Other objects and advantages of the present invention will become apparent from the detailed description to follow taken in conjugation with the appended claims and drawings.

Figure 1A:
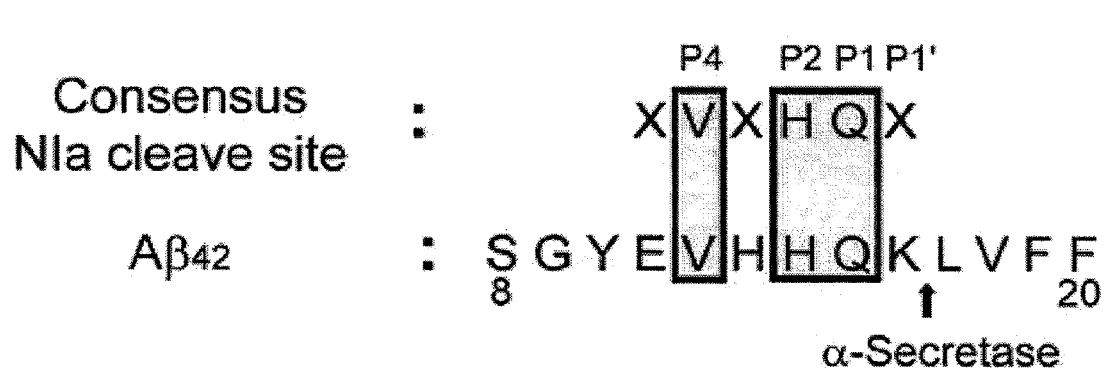
FIGS. 1A-1D. Cleavage of Aβ by NIa.

(A) The amino acid sequence of Aβ is aligned with the consensus cleavage site of NIa, Val-Xaa-His-Gln. (B) NIa was purified from E. coli and separated by SDS-PAGE. Lane 1, molecular size markers; lane 2, NIa (10 μg). (1C) Monomeric Aβ (2.5 μM) was incubated with NIa (1.5 μM) in the presence or absence of NEM for 3 hrs at 25° C. The reaction mixture was separated on a Tris-tricine gel, blotted, and probed with the anti-Aβ antibody, 6E10. The density of each Aβ band was quantified by densitometry. The band intensities after 3 hr incubation (lanes 2, 4, and 6) were plotted relative to the band intensities of each sample at 0 hr (lanes 1, 3, and 5). n=4. (D) Oligomeric Aβ (2.5 μM) was incubated with NIa (1.5 μM) in the presence or absence of NEM for 3 hrs at 25° C. The reaction mixture was separated and immunoblotted with anti-Aβ antibody, 6E10. The density of oligomeric Aβ bands was quantified by densitometry. The band intensities of oligomeric Aβ after 3 hr incubation (lanes 2, 4, and 6) were plotted relative to the band intensity of the Aβ only sample at the 3 hr incubation time point (lane 2). n=4. Error bars represent SD. *p<0.05 and **p<0.01.

Figure 2A:
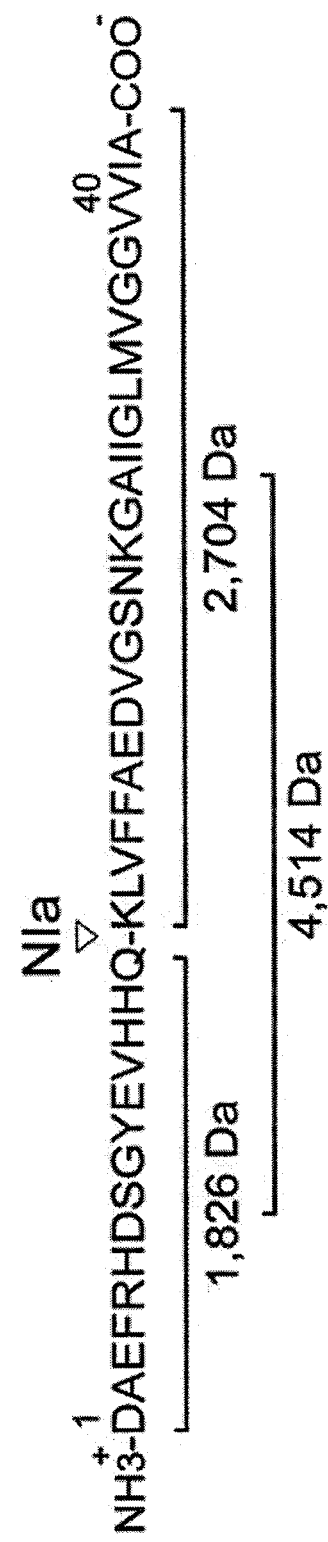
Figure 2B:
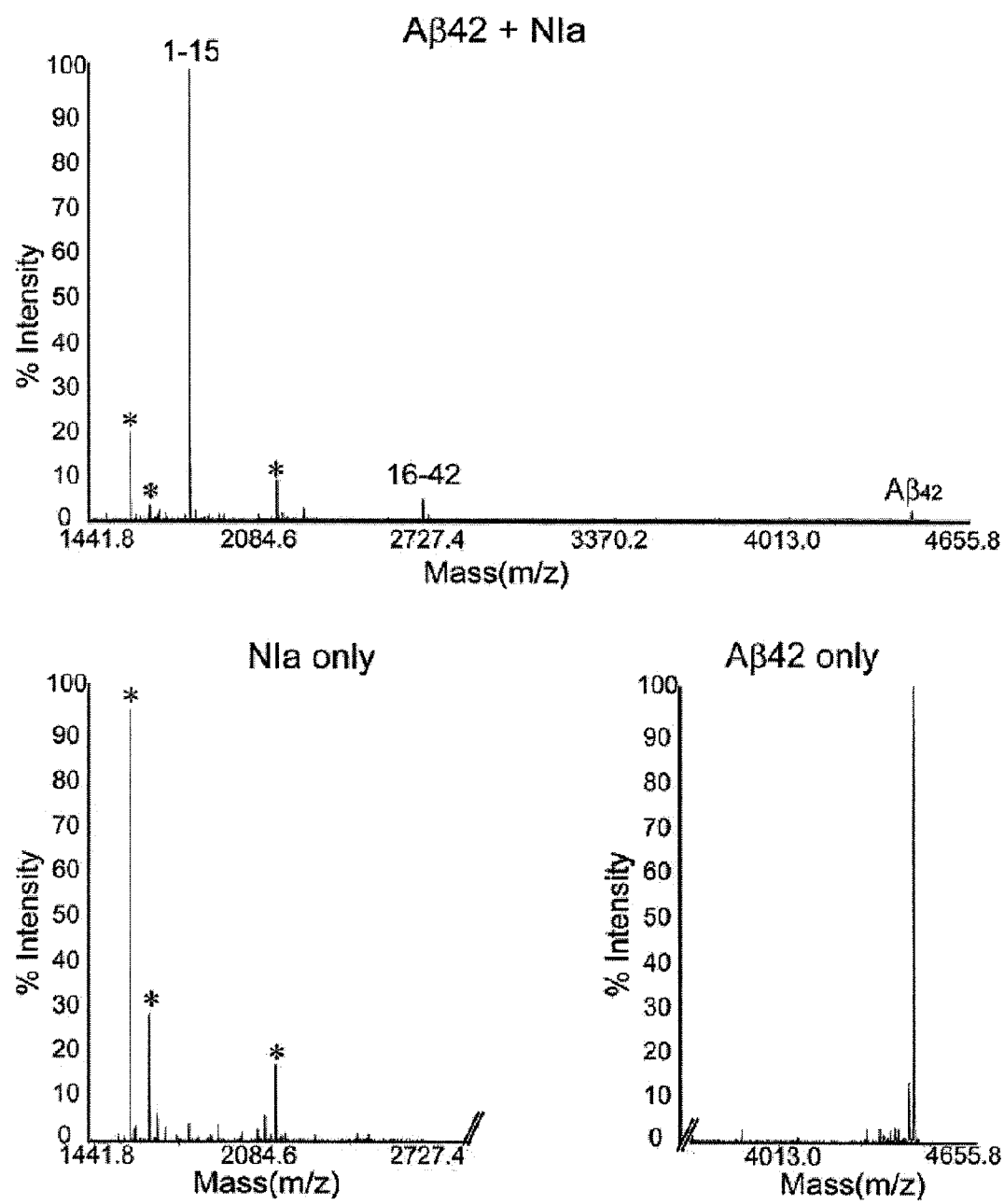

FIGS. 2A-2B. Mass spectra of monomeric Aβ incubated with NIa.

(A) The calculated molecular masses of the expected cleavage products are shown. (B) Monomeric Aβ (2.5 μM) was incubated with NIa (1.5 μM) for 3 hrs at 25° C. and analyzed using MALDI-TOF/TOF mass spectrometry. Note that two peaks corresponding to the Aβ cleavage products as well as a peak corresponding to Aβ were detected. As controls, NIa and Aβ were analyzed separately. Three minor peaks marked by asterisks represent contamination of the NIa preparation.

Figure 3A:
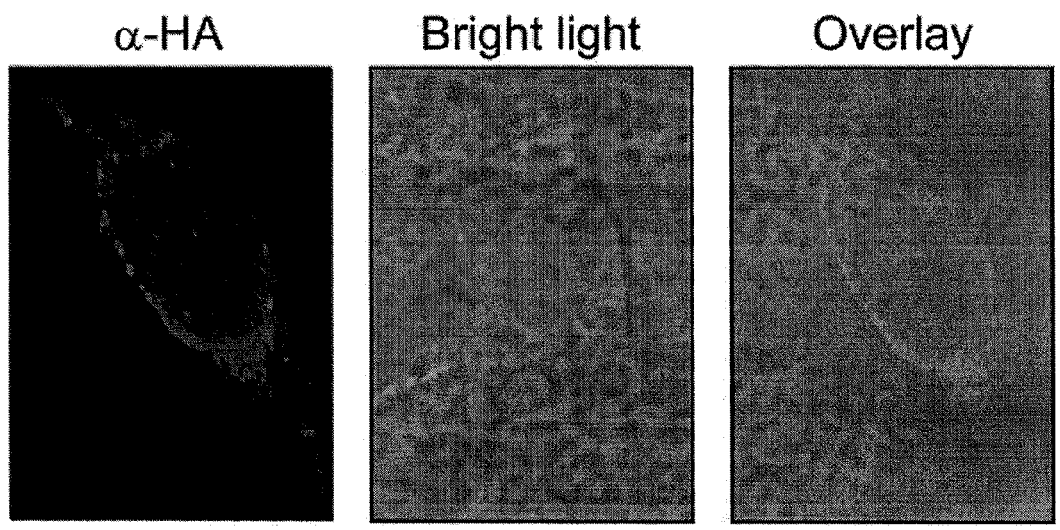
Figure 3B:
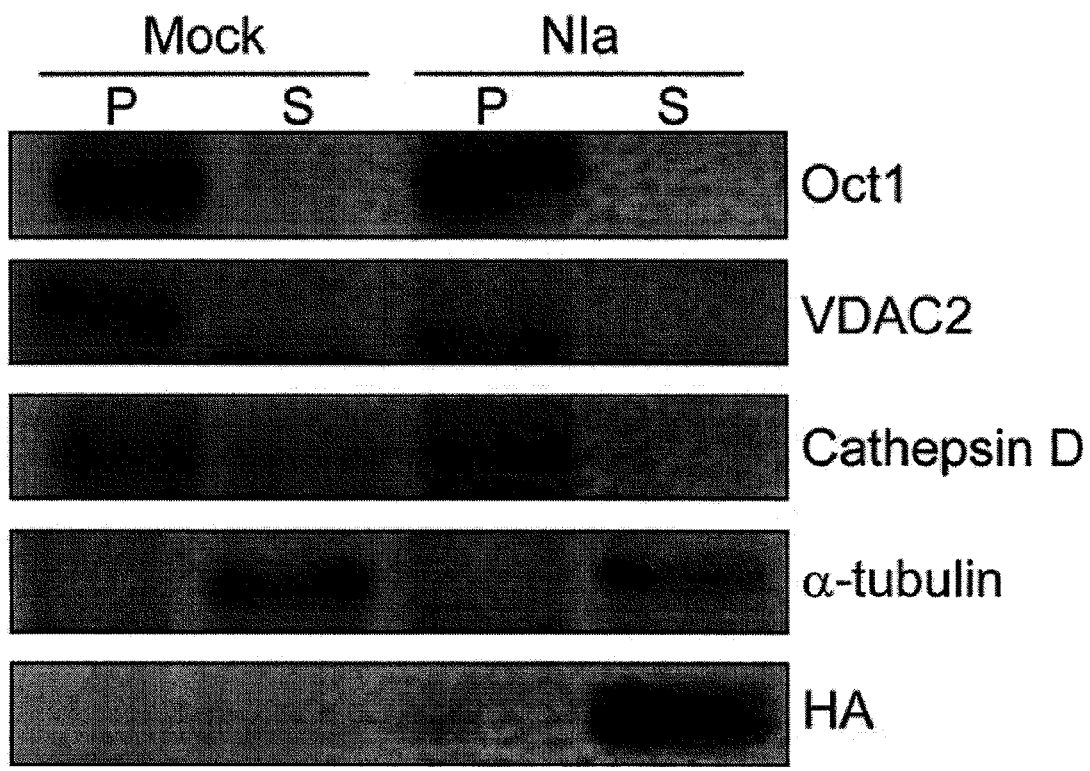

FIGS. 3A-3B. Subcellular localization of NIa in B103 neuroblastoma cells.

(A) B103 neuroblastoma cells transformed with pcDNA-HA-NIa were immunostained with anti-HA antibody and observed under a confocal microscope. (B) B103 cells transformed with a blank plasmid (Mock) or pcDNA-HA-NIa (NIa) were fractionated into particulate (P) and soluble (S) fractions by differential centrifugation. The two fractions were separated by SDS-PAGE, blotted, and probed with antibodies against Oct1 (nuclear), VDAC2 (mitochondrial), cathepsin D (lysosomal), α-tubulin (cytosolic), and HA (NIa).

Figure 4A:
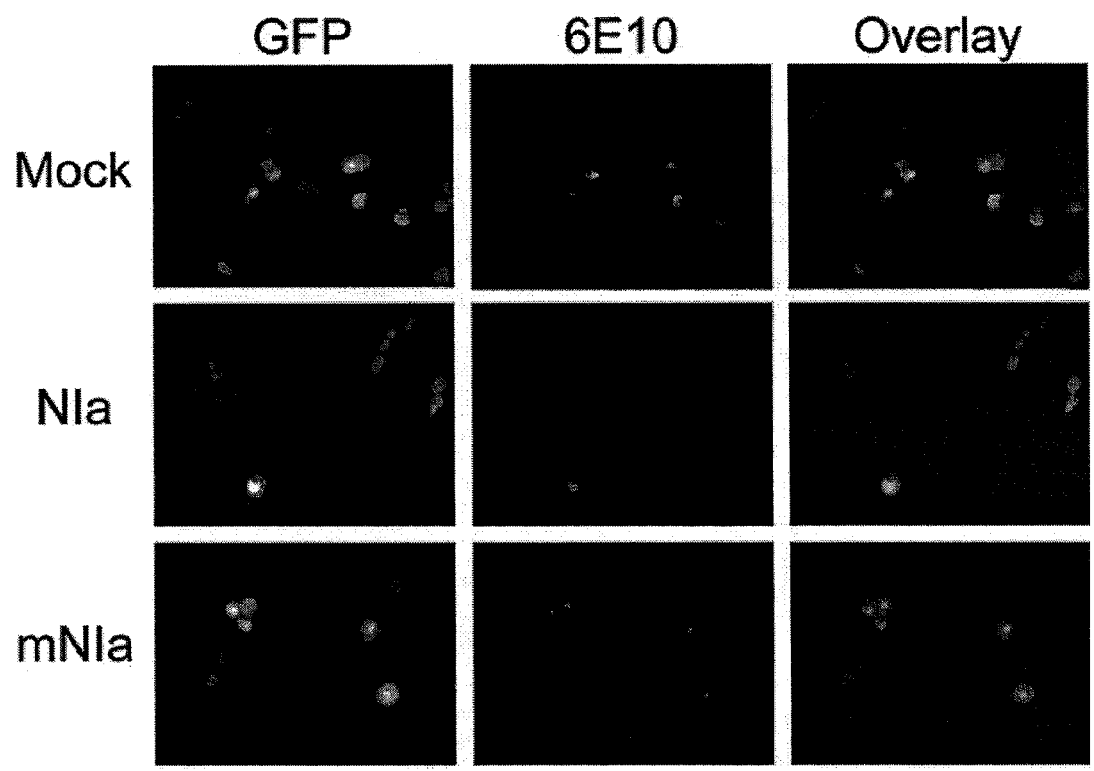
Figure 4B:
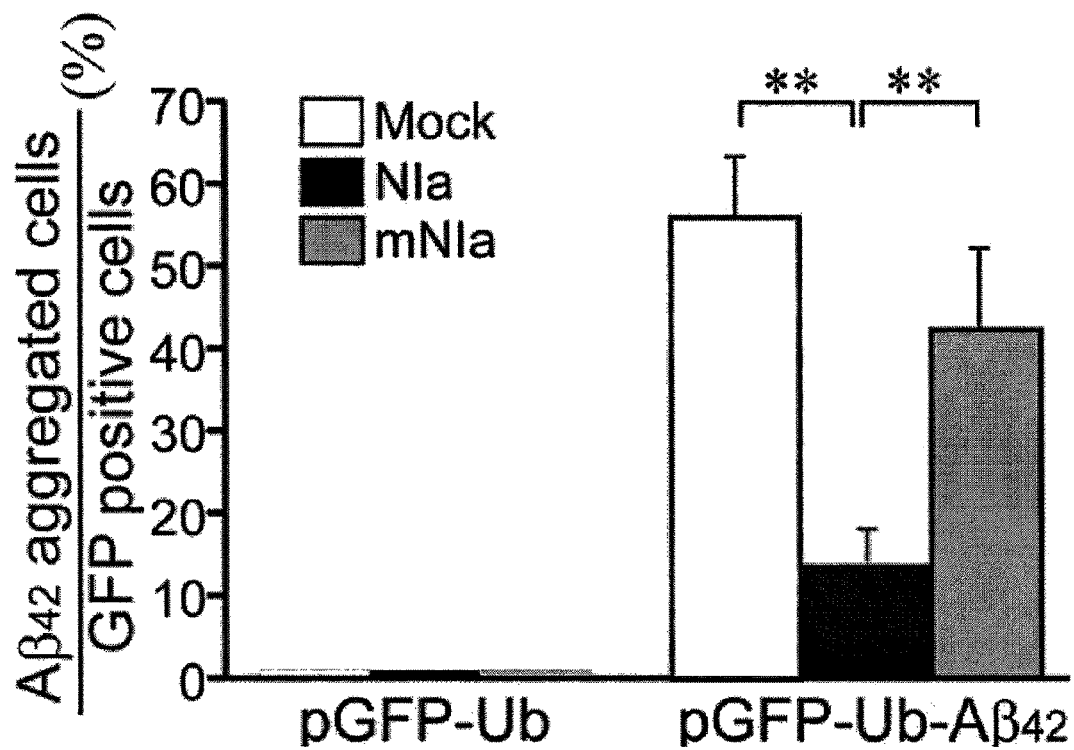
Figure 4C:
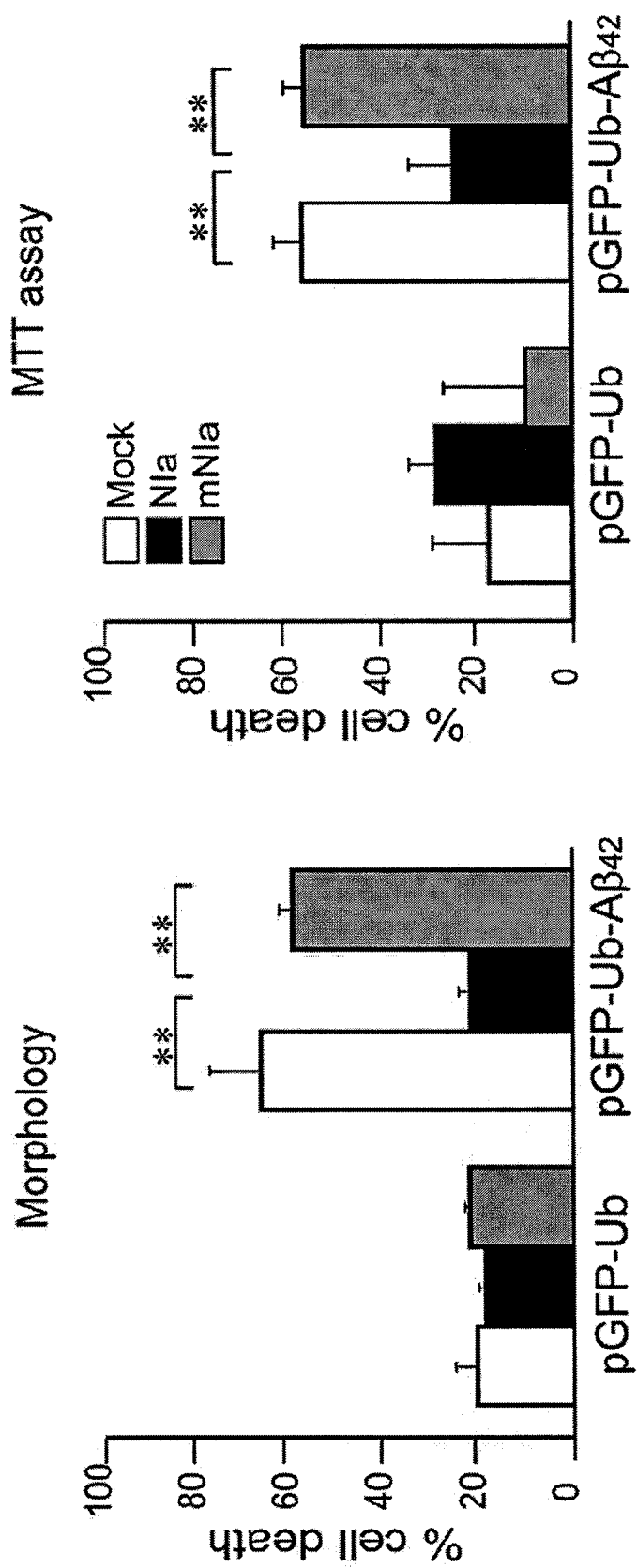

FIGS. 4A-4C. Degradation of intracellular Aβ and inhibition of intracellular Aβ-induced cell death by NIa.

(A) B103 neuroblastoma cells were cotransfected with pGFPUb-Aβ and an empty vector (Mock), pcDNA-HA-NIa (NIa), or pcDNA-HA-mNIa (mNIa). After 48 hrs of incubation, the cells were immunostained with the anti-Aβ antibody, 6E10. (B) The number of Aβ-positive cells (red) and GFP-expressing cells (green) were counted under the microscope and their ratio was calculated. n=6. (C) Cell death induced by intracellular Aβ peptide was measured by morphological and MTT assays. n=6. Error bars represent SD. **p<0.01.

Figure 5:
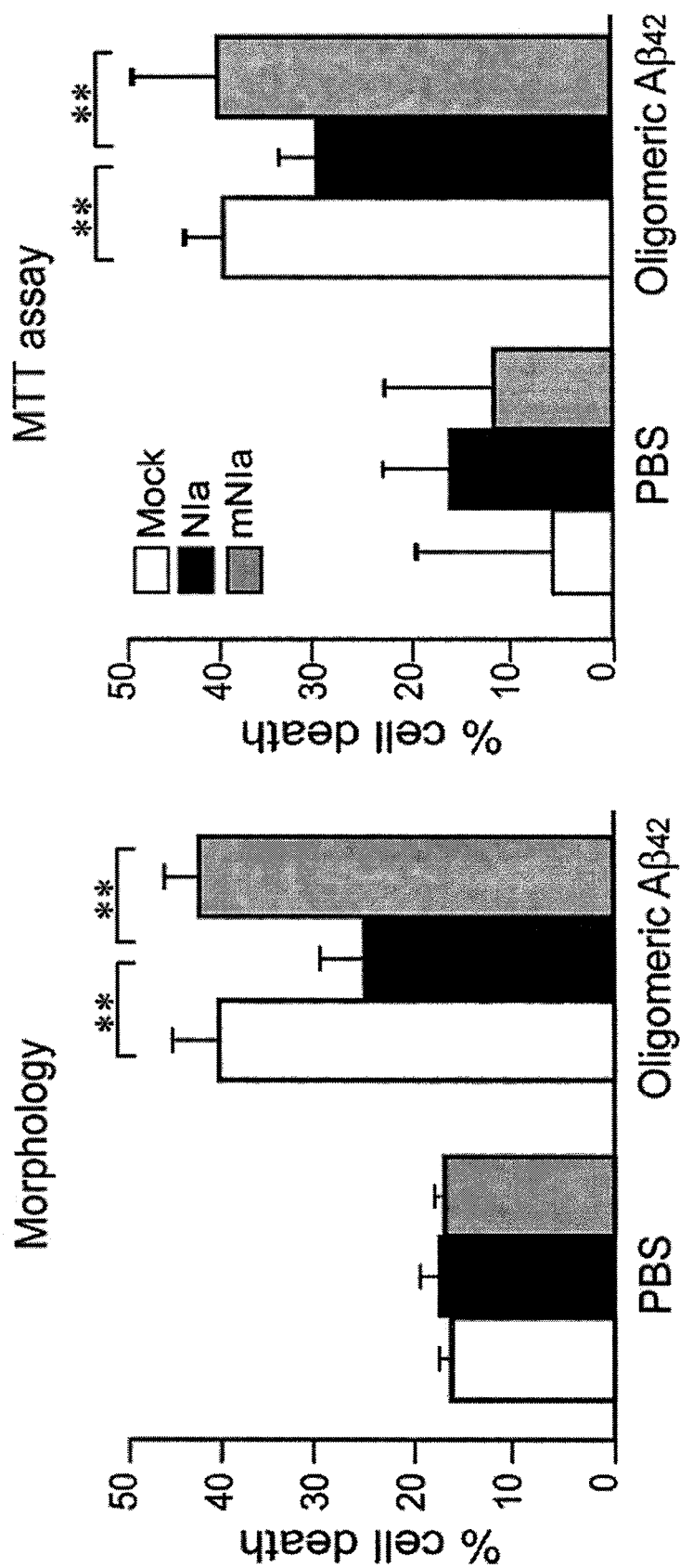

FIG. 5. Inhibition of exogenously added Aβ-induced cell death by NIa.

B103 neuroblastoma cells transfected with an empty vector (Mock), pcDNA-HA-NIa (NIa), or pcDNA-HA-mNIA (mNIa) were treated with Aβ (5 μM) in culture media for 48 hrs. Cell death was measured by morphological and MTT assays. n=6. Error bars represent SD. **p<0.01.

FIGS. 6A-6D. Lentiviral-mediated expression of NIa.

(A) Lentiviral constructs for the expression of HA-NIa and GFR (B) Western blotting with anti-HA antibody showed the NIa expression levels in 293T cells infected with Lenti-NIa. (C) The expression of NIa in mouse brains was detected by immunohistochemistry with anti-HA antibody and anti-mouse-FITC secondary antibody. The prefrontal sections of mouse brains infused with Lenti-NIa are compared with the brain sections of control non-injected mice. (D) The brains infused with Lenti-GFP and Lenti-NIa were subjected to RT-PCR. A PCR product corresponding to NIa was detected. GAPDH was used as control. CMV, Cytomegalovirus RNA polymerase II promoter; WPRE, Woodchuck hepatitis post-transcriptional regulatory element; U5, HIV 5'-long terminal repeat; Δ U3, 3' self inactivating long terminal repeat; PSI, region of viral RNA responsible for directing packaging; PRE, binding site for the Rev protein that aids in the transport of unspliced RNAs from the nucleus to cytoplasm.

Figure 7A:
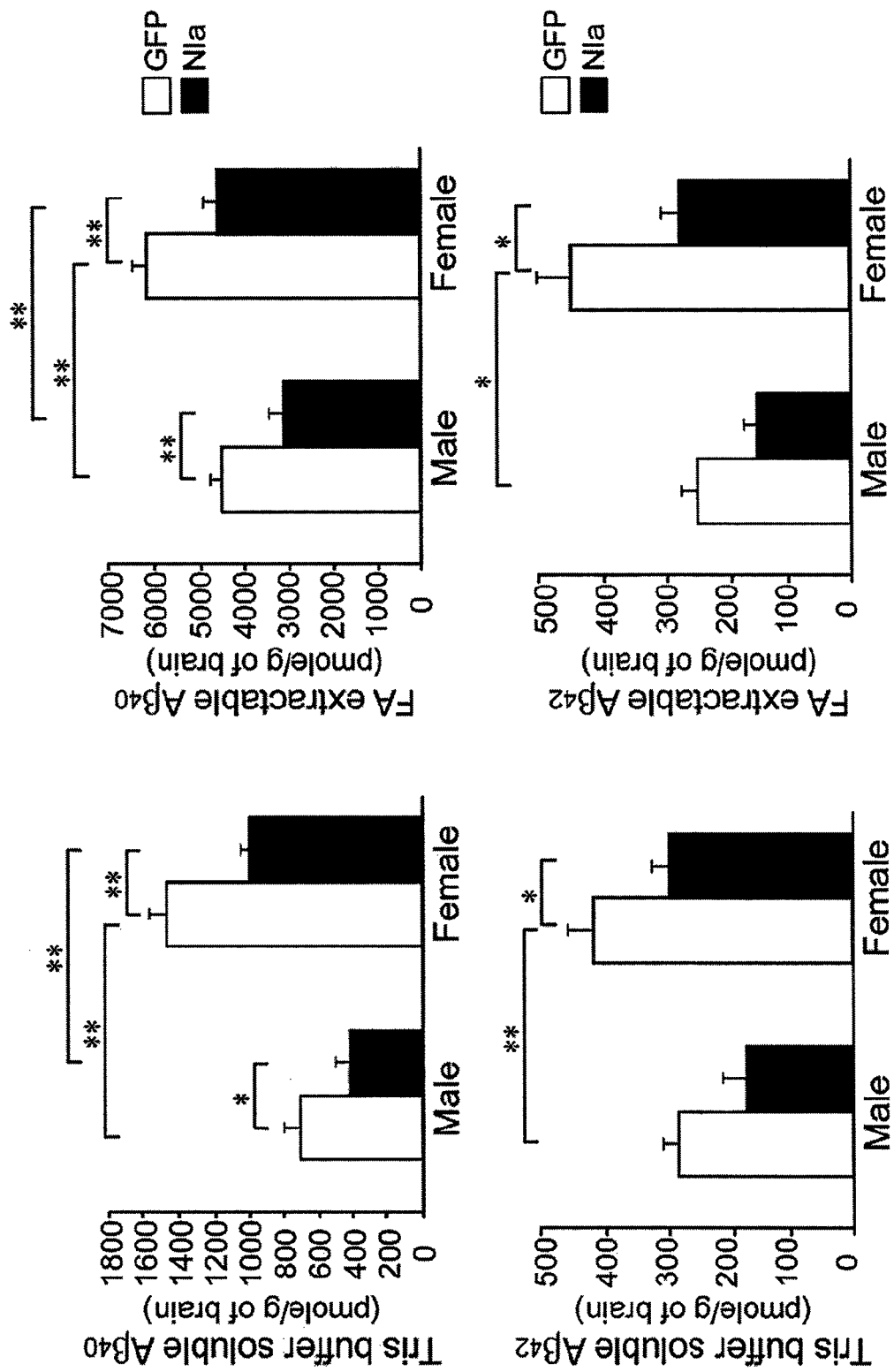
Figure 7B:
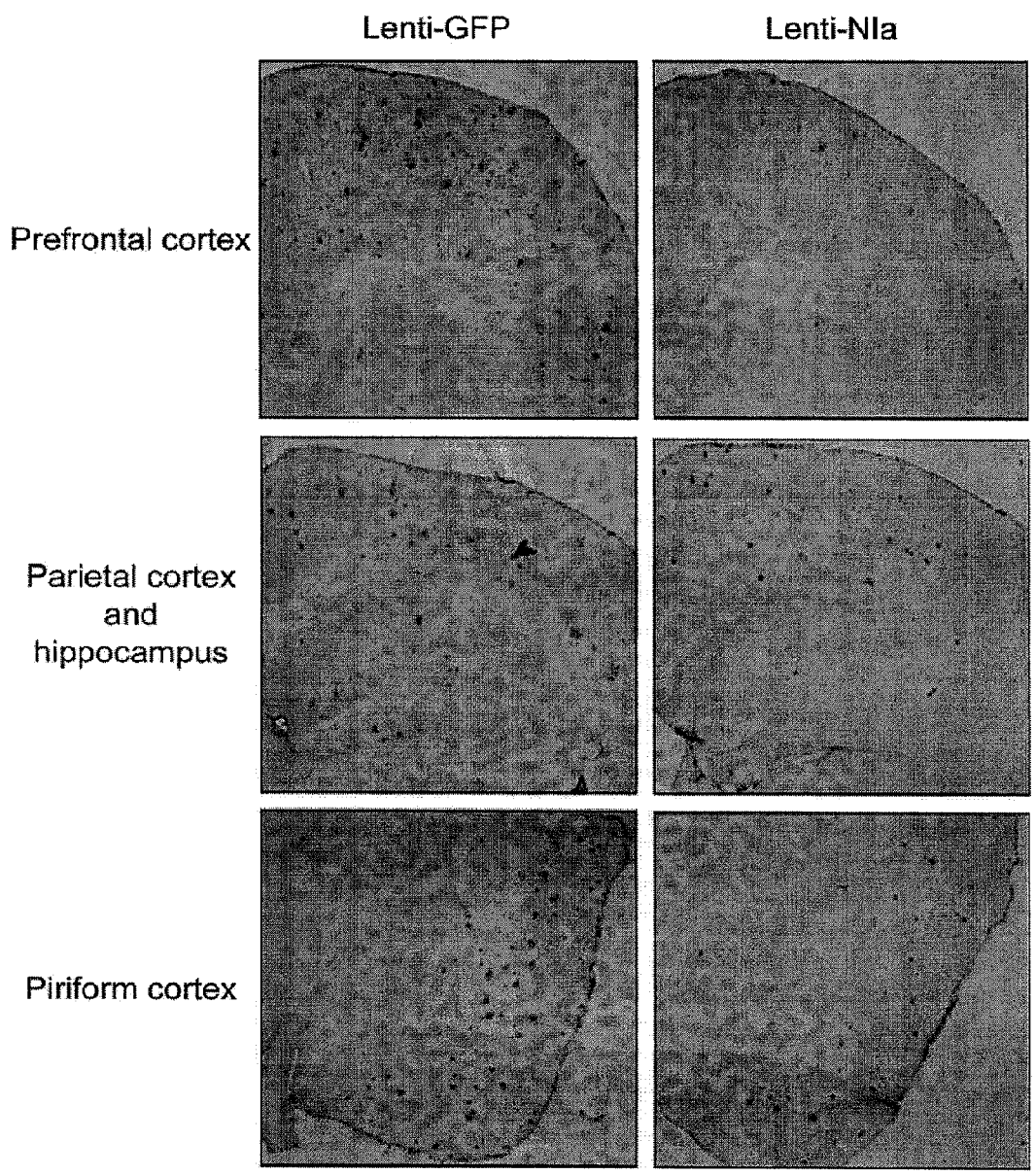
Figure 7C:
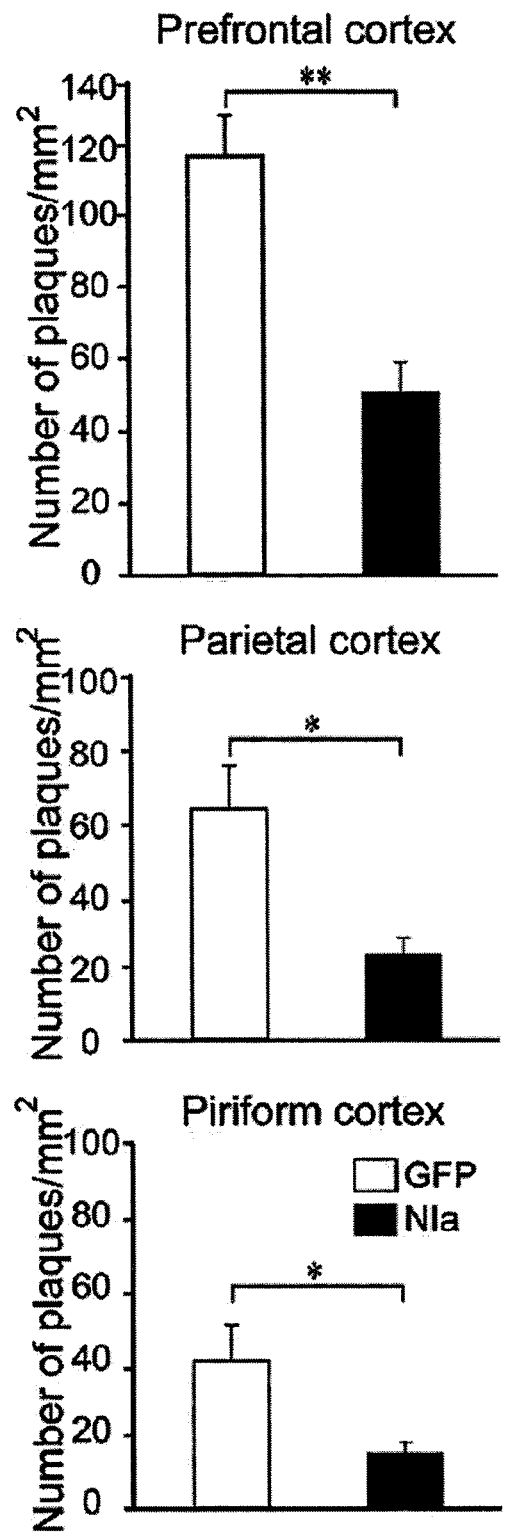

FIGS. 7A-7C. NIa-mediated reduction in Aβ levels and Aβ plaques in APPsw/PS1dE9 mouse brains.

(A) Brains of APPsw/PS1dE9 were bilaterally infused with Lenti-GFP and Lenti-NIa, and the amounts of $A\beta_{1-40}$ and $A\beta_{1-42}$ were measured by ELISA. The amounts of soluble and insoluble $A\beta_{1-40}$ are shown (upper lane). The amounts of soluble and insoluble $A\beta_{1-42}$ are shown (lower lane). (B) Sections of prefrontal cortex, parietal cortex, hippocampus, and piriform cortex of APPsw/PS1dE9 male mouse infused with Lenti-GFP and Lenti-NIa were stained with anti-Aβ antibody (Barn-10). (C) The number of plaques in the prefrontal cortex, parietal cortex, and piriform cortex of APPsw/PS1dE9 male mouse infused with Lenti-GFP and Lenti-NIa was counted. For Lenti-GFP infusions, n=5 for male and n=5 for female. For Lenti-NIa infusions, n=6 for male and n=3 for female. Error bars represent SD. *p<0.05 and **p<0.01.

DETAILED DESCRIPTION OF THIS INVENTION

In one aspect of the present invention, there is provided a pharmaceutical composition for preventing or treating an amyloid β-caused disease, which comprises as an active ingredient a NIa (nuclear inclusion a) protease or a gene carrier containing a nucleotide sequence encoding the NIa protease.

In another aspect of the present invention, there is provided a method for preventing or treating an amyloid β-caused disease, which comprises administering to a mammalian subject the pharmaceutical composition described above.

The present inventors have made intensive endeavors to develop proteolytic therapeutics for amyloid β-caused diseases, inter alia, Alzheimer's disease. As a result, we have discovered that the nuclear inclusion a (NIa) protease of Turnip mosaic virus (TuMV) cleaves monomeric and oligomeric amyloid β (Aβ) in an effective and specific manner and significantly prevents the Aβ-induced cell death in neuronal culture cells and the Aβ-related pathology in transgenic AD (Alzheimer's disease) mice. NIa might therefore provide a novel strategy for the clearance of toxic oligomeric Aβ from the brain of AD patients.

The nuclear inclusion a (NIa) protease of turnip mosaic virus (TuMV) is responsible for the processing of the viral polyprotein into functional proteins. NIa was previously shown to possess a relatively strict substrate specificity with a preference for Val-Xaa-His-Gln↓, with the scissile bond located after Gln. The presence of the same consensus sequence, $Val^{12}$-His-His-$Gln^{15}$, near the presumptive α-secretase cleavage site of the amyloid-β (Aβ) peptide led us to hypothesize that NIa could possess activity against Aβ.

According to a preferred embodiment, the NIa protease has the activity to cleave an oligomeric Aβ as well as a monomeric Aβ. As well known to one of skill in the art, the oligomeric Aβ is shown to be approximately 10- and 40-fold more cytotoxic than fibrillar and monomeric Aβ, respectively. A dimeric Aβ are 3-fold more toxic than monomeric Aβ, and trimeric and tetrameric Aβ are upto 13-fold more toxic. In this regard, the NIa protease used in this invention is very advantageous for treating AD by clearing more toxic Aβ molecules.

According to a preferred embodiment, the NIa protease cleaves intracellular or extracellular Aβ. More preferably, the NIa protease used in this invention cleaves Aβ present in cytosol. As demonstrated in Example, the expression of NIa in neuronal cells inhibits cell death induced both by intracellularly expressed and exogenously added Aβ. In addition, lentiviral-mediated overexpression of NIa in the brain of AD transgenic mice reduces the levels of Aβ and plaque formation. These data provide additional evidence supporting a critical role for intracellular Aβ in the pathogenesis of AD. In this regard, NIa could be used as a novel tool to study the molecular events underlying the induction of cell death by intracellular Aβ. Moreover, the present invention offers proof-of-concept that the clearance of intracellular Aβ by a cytosolic protease could be a viable strategy for the treatment of AD.

According to a preferred embodiment, the NIa protease inhibits the amyloid β-induced cell death.

According to a preferred embodiment, the NIa protease has the activity to cleave amyloid $beta_{1-40}$ and amyloid $beta_{1-42}$.

According to a preferred embodiment, the NIa protease has the activity to cleave a peptide bond between amino acids 15 and 16 of SEQ ID NO:3.

The NIa protease used in the present invention may be provided as a protein or a gene carrier containing a nucleotide sequence encoding the NIa protease.

Where the NIa protease is provided in the form of a protein, it may be alternatively fused to a protein transduction domain (PTD) for effectively penetrating into cells. The preferable amino acid sequence of the NIa protease is set forth as SEQ ID:1.

The protein transduction domain useful in the present invention includes, but not limited to, HIV TAT, VP-22, a growth factor signal peptide sequence, Pep-1, Pep-7, a Drosophila Antp peptide, oligoarginine, HSV VP22 transcription regulatory protein, vFGF-derived MTS peptide, Penetratin, Transportan, Buforin II, MAP (model amphiphatic peptide), k-FGF, Ku 70, pVEC, SynB1 and HN-1.

Where the NIa protease is provided as a gene carrier for clearing Aβ, it may be constructed in a gene carrier in accordance with conventional technologies known to one of skill in the art.

The term "gene carrying" used herein refers to the transfer of gene into cells and has the same meaning as gene delivery.

To construct the present gene carrier, it is preferred that the NIa protease-encoding nucleotide sequence is contained in a suitable expression construct. According the expression construct, it is preferred that the NIa protease-encoding nucleotide sequence is operatively linked to a promoter. The term "operatively linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence. According to the present invention, the promoter linked to the NIa protease gene is operable in, preferably, animal, more preferably, mammalian cells, to control transcription of the NIa protease gene, including the promoters derived from the genome of mammalian cells or from mammalian viruses, for example, CMV (cytomegalovirus) promoter, the adenovirus late promoter, the vaccinia virus 7.5K promoter, SV40 promoter, HSV tk promoter, RSV promoter, EF1 alpha promoter, metallothionein promoter, beta-actin promoter, human IL-2 gene promoter, human IFN gene promoter, human IL-4 gene promoter, human lymphotoxin gene promoter and human GM-CSF gene promoter. Most preferably, the promoter is CMV promoter.

Preferably, the expression construct used in this invention comprises a polyadenylation sequence (e.g., bovine growth hormone terminator and SV40-derived polyadenylation sequence).

According to a preferred embodiment, the expression construct for the NIa protease-encoding nucleotide sequence has a structure of "promoter-NIa protease-encoding nucleotide sequence-polyadenylation sequence.

The gene carrier of the present invention is constructed in a variety of forms, preferably, (i) naked recombinant DNA molecule, (ii) plasmid, (iii) viral vector, or (iv) liposome or neosome containing naked recombinant DNA molecule and plasmid.

The NIa protease-encoding nucleotide sequence may be applied to a multitude of gene carriers useful in gene therapy, preferably, plasmid, adenovirus[22], adeno-associated virus (AAV, Lashford L S., et al., Gene Therapy Technologies, Applications and Regulations Ed. A. Meager, 1999), retrovirus[23], herpes simplex virus[24], vaccinia virus[25], liposome (Methods in Molecular Biology, Vol 199, S. C. Basu and M. Basu (Eds.), Human Press 2002) or neosome. Most preferably, the gene carrier of this invention is constructed by incorporating the NIa protease-encoding nucleotide sequence to retrovirus or lentivirus.

(i) Adenovirus

Adenovirus has been usually employed as a gene carrier because of its mid-sized genome, ease of manipulation, high titer, wide target-cell range, and high infectivity. Both ends of the viral genome contains 100-200 bp LTRs (inverted terminal repeats), which are cis elements necessary for viral DNA replication and packaging. The E1 region (E1A and E1B) encodes proteins responsible for the regulation of transcription of the viral genome and a few cellular genes. The expression of the E2 region (E2A and E2B) results in the synthesis of the proteins for viral DNA replication.

Of adenoviral vectors developed so far, the replication incompetent adenovirus having the deleted E1 region is usually used. The deleted E3 region in adenoviral vectors may provide an insertion site for transgenes[25,26]. Therefore, it is preferred that the NIa protease-encoding nucleotide sequence is inserted into either the deleted E1 region (E1A region and/or E1B region, preferably, EIB region) or the deleted E3 region, more preferably, the deleted E3 region. The promoter-NIa protease gene-poly A sequence is preferably present in either the deleted E1 region (E1A region and/or E1B region, preferably, EIB region) or the deleted E3 region, more preferably, the deleted E3 region.

In nature, adenovirus can package approximately 105% of the wild-type genome, providing capacity for about 2 extra kb of DNA[27]. In this regard, the foreign sequences described above inserted into adenovirus may be further inserted into adenoviral wild-type genome.

The adenovirus may be of any of the 42 different known serotypes or subgroups A-F. Adenovirus type 5 of subgroup C is the most preferred starting material for constructing the adenoviral gene carrier of this invention. A great deal of biochemical and genetic information about adenovirus type 5 is known.

The foreign genes delivered by the present adenoviral gene carrier are episomal, and therefore, have low genotoxicity to host cells. Therefore, gene therapy using the adenoviral gene carrier of this invention may be considerably safe.

(ii) Retrovirus or Lentivirus

Retroviruses or lentiviruses[23] capable of carrying relatively large exogenous genes have been used as viral gene delivery vectors in the senses that they integrate their genome into a host genome and have broad host spectrum.

In order to construct a retroviral vector or lentiviral vector, the NIa protease-encoding nucleotide sequences to be transferred are inserted into the viral genome in the place of certain viral sequences to produce a replication-defective virus. To produce virions, a packaging cell line containing the gag, pol and env genes but without the LTR (long terminal repeat) and ψ components is constructed[28]. When a recombinant plasmid containing the NIa protease-encoding sequence, LTR and ψ is introduced into this cell line, the ψ sequence allows the RNA transcript of the recombinant plasmid to be packaged into viral particles, which are then secreted into the culture media Nicolas and Rubinstein "Retroviral vectors," In: Vectors: A survey of molecular cloning vectors and their uses, Rodriguez and Denhardt[29]. The media containing the recombinant retroviruses is then collected, optionally concentrated and used for gene delivery.

A successful gene transfer using the second-generation retroviral vector has been reported. Kasahara et al.[30] prepared variants of moloney murine leukemia virus in which the EPO (erythropoietin) sequence is inserted in the place of the envelope region, consequently, producing chimeric proteins having novel binding properties. Likely, the present gene carrier can be constructed in accordance with the construction strategies for the second-generation retroviral vector.

(iii) AAV Vector

Adeno-associated viruses are capable of infecting non-dividing cells and various types of cells, making them useful in constructing the gene carrier of this invention. The detailed descriptions for use and preparation of AAV vector are found in U.S. Pat. Nos. 5,139,941 and 4,797,368.

Research results for AAV as gene carriers are disclosed in LaFace et al.[31], Zhou et al.[32], Walsh et al.[33] and Flotte et al.[34] Recently, an AAV vector has been approved for Phase I human trials for the treatment of cystic fibrosis.

Typically, a recombinant AAV virus is made by cotransfecting a plasmid containing the gene of the NIa protease flanked by the two AAV terminal repeats[35,36] and an expression plasmid containing the wild type AAV coding sequences without the terminal repeats[37].

(iv) Other Viral Vectors

Other viral vectors may be employed as a gene carrier in the present invention. Vectors derived from viruses such as vaccinia virus[25]; Ridgeway, "Mammalian expression vectors," In: Vectors: A survey of molecular cloning vectors and their uses. Rodriguez and Denhardt[29]; Baichwal and Sugden, "Vectors for gene transfer derived from animal DNA viruses: Transient and stable expression of transferred genes," In: Kucherlapati R, ed. Gene transfer[38] (New York: Plenum Press, 117-148 (1986)) and herpes simplex virus[24] may be used in the present delivery systems for transferring both the NIa protease gene into cells.

(v) Liposome

Liposomes are formed spontaneously when phospholipids are suspended in an excess of aqueous medium. Liposome-mediated nucleic acid delivery has been very successful as described in Nicolau and Sene[39] and Nicolau et al.[40] Example of commercially accessible reagents for transfecting animal cells using liposomes includes Lipofectamine (Gibco BRL). Liposomes entrapping the NIa protease gene interact with cells by mechanism such as endocytosis, adsorption and fusion and then transfer the sequences into cells.

In another aspect of this invention, there is provided a method for delivery a gene, which comprises contacting the gene carrier of this invention as described hereinabove to a biosample containing cells.

Where the present gene carrier is constructed on the basis of viral vector construction, the contacting is performed as conventional infection methods known in the art. The infection of hosts using viral vectors is well described in the above-cited publications.

Where the present gene carrier is a naked recombinant DNA molecule or plasmid, the NIa protease-encoding sequence and nucleotide sequence to be delivered are introduced into cells by microinjection[41,42], calcium phosphate co-precipitation[43,44], electroporation[45,46], liposome-mediated, transfection[47,39,40], DEAE-dextran treatment[48] and particle bombardment[49].

According to a preferred embodiment, the NIa protease gene (e.g., SEQ ID NO:2) is carried in a viral vector, more preferably a retroviral vector or lentiviral vector.

In the pharmaceutical compositions of this invention, the pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propyl hydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in Remington's Pharmaceutical Sciences (19th ed., 1995), which is incorporated herein by reference.

The pharmaceutical composition of this invention may be preferably administered parenterally. For non-oral administration, local injection, intrathecal injection, intravenous injection or intraperitoneal injection may be employed.

A suitable dose of the pharmaceutical composition of the present invention may vary depending on pharmaceutical formulation methods, administration methods, the patient's age, body weight, sex, severity of diseases, diet, administration time, administration route, an excretion rate and sensitivity for a used pharmaceutical composition. Physicians of ordinary skill in the art can determine an effective amount of the pharmaceutical composition for desired treatment. Preferably, the pharmaceutical composition of the present invention is administered with a daily dose of 0.001-1000 mg/kg (body weight).

According to the conventional techniques known to those skilled in the art, the pharmaceutical composition may be formulated with pharmaceutically acceptable carrier and/or vehicle as described above, finally providing several forms including a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

The pharmaceutical composition of this invention may be employed to prevent or treat a variety of diseases or disorders, including Alzheimer's disease, MCI (mild cognitive impairment), mild-to-moderate cognitive impairment, vascular dementia, cerebral amyloid angiopathy, hereditary cerebral hemorrhage, senile dementia, Down's syndrome, inclusion body myositis, age-related macular degeneration and conditions associated with Alzheimer's disease. In particular, the pharmaceutical composition of this invention is a promising therapeutic for Alzheimer's disease.

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods
Antibodies and Reagents

Cell culture reagents were purchased from GIBCO-BRL (Invitrogen, Carlsbad, Calif., USA). Synthetic $A\beta_{1-42}$ peptide was purchased from Sigma (St Louis, Mo., USA) and Anygen (Gwangju, Korea). 6E10 antibody recognizing residues 1-17 of Aβ peptide was purchased from Signet™ (Dedham, Mass., USA). Antibodies against HA, α-tubulin, VDAC2, Oct1, and cathepsin D were purchased from Abcam (Cambridge, Mass., UK). Chitin beads were purchased from New England BioLabs (Ipswich, Mass., USA). All other reagents were purchased from Sigma.

Purification of the NIa Protease

To produce recombinant NIa protein in E. coli, the NIa gene was cloned into pTYB12 (New England BioLabs) via the EcoRI and XhoI sites. The pTYB12 vector contains an N-terminal intein tag. The pTYB12-NIa vector was transformed into the E. coli strain BL21 (DE3) and grown at 37° C. in LB medium. Induction of the NIa protein was achieved by addition of 400 μM IPTG overnight at 20° C. The cells were harvested, resuspended in column buffer (20 mM HEPES [pH 7.9], 500 mM NaCl, 1 mM EDTA), and lysed by sonication. The lysate was centrifuged and the resulting supernatant was loaded onto a chitin column equilibrated with column buffer. After extensive washing, the NIa protein was eluted from the column using a column buffer containing 50 mM DTT, dialyzed in storage buffer (50 mM HEPES [pH 7.6], 1 mM EDTA, 1 mM DTT, 10% glycerol), and concentrated by Amicon Centriprep (Millipore, Billerica, Mass., USA). The protein concentration was determined by the BCA method and analyzed on a 12% SDS-PAGE gel.

Aβ Preparation

To prepare Aβ solutions, we followed the method described by Yan et al.[50] and Dahlgren et al.[3]. Synthetic human $A\beta_{1-42}$ peptides (>95% pure by high performance liquid chromatography and mass spectrometry tests) were dissolved in dimethylsulfoxide (DMSO) to a concentration of 5 mM. For monomeric Aβ, the Aβ solution in DMSO was diluted in PBS to a final concentration of 25 μM immediately before use. For oligomeric Aβ, the Aβ solution in DMSO was diluted in PBS to a is concentration of 100 μM and incubated at 4° C. for 36 hrs. The physical state of Aβ was confirmed by PAGE with 10-20% Tris-Tricine gels (Bio-Rad, Hercules, Calif., USA).

Cleavage Assays and Mass Spectrometry 1.5 μM of the recombinant NIa protease was incubated with 2.5 μM Aβ preparations in an assay buffer (HEPES [pH 7.4], 20 mM KCl, 20 mM MgCl2) at 25° C. for 3 hrs. As a control, the NIa protease was pre-incubated with the cysteine protease inhibitor, N-ethylmaleimide (NEM) for 10 min at 4° C. After incubation, the mixtures were subjected to PAGE with 10-20% Tris-Tricine gel and Western blotting using the anti-Aβ antibody 6E10. To further analyze the cleavage products, the reaction mixtures were analyzed by MALDI-TOF/TOF mass spectrometry (4700 Proteomics Analyzer, Applied Biosystems, Carlsbad, Calif., USA). As controls, NIa and Aβ were separately analyzed.

Cell Culture, Transfection and Aβ Treatment

B103 rat neuroblastoma cells were cultured in DMEM supplemented with 10% (vol/vol) fetal bovine serum[51]. A mutant NIa gene in which $Asp^{81}$ in the catalytic triad was changed to Ala was generated by a PCR mutagenesis. To express the wild type and mutant NIa in B103 cells, the corresponding genes were subcloned into pcDNA3 (Invitrogen) containing an N-terminal HA tag. Cells were transfected using Lipofectamine Reagent (Invitrogen) according to the manufacturer's protocol. A cytosolic $A\beta_{1-42}$ expression vector (pGFPUb-$A\beta_{1-42}$) was previously described[52]. For the Aβ treatment, the Aβ solutions (100 μM) were added to a final concentration of 5 μM.

Assessment of Cell Death

Cell viability was assessed by MTT assay and cell morphological methods. The 3-[4,5-dimethylthizaol-2-yl]-2,5-diphenyl tetrazolium bromide (MTT) was solubilized in PBS to 5 mg/ml. A volume of MTT solution equal to 10% of the culture media volume was added to the cell culture at 37° C. for 3 hrs. A solubilization solution (10% Triton X-100 and 0.1 N HCl in anhydrous isopropanol) in a volume equal to the culture media volume was added and further incubated at 37° C. until the resulting formazan crystals were completely dissolved. The absorbance of the samples was measured at 570 nm, and the background absorbance of each well was measured at 690 nm. For the assessment of cell morphology, cultured cells were co-transformed with the experimental plasmid and a GFP plasmid and the morphology of GFP-positive cells was examined under a fluorescence microscope42 (Olympus, Shinjuku, Tokyo, Japan).

Immunofluorescence and Confocal Microscopy

B103 rat neuroblastoma cells were washed with PBS containing 1 mM $CaCl_2$ and 1 mM $MgCl_2$ and fixed for 10 min with 3.5% paraformaldehyde. The cells were permeabilized by incubation with 0.2% Triton X-100 in PBS for 10 min, blocked with 5% BSA in PBS for 1 hr, and incubated with anti-6E10 monoclonal antibody or HA monoclonal antibody for 1 hr.

The fixed cells were then rinsed in PBS and incubated with Alexa 488 fluor-conjugated secondary antibody (Invitrogen) and TRITC-conjugated secondary antibody (Jackson Immunoresearch, West Grove, Pa., USA) for 1 hr. For immunofluorescence microscopy, immunoreactivity was captured with a fluorescence microscope (Olympus) with a ProgRes $C10^{plus}$ camera (JENOPTIK, Goeschwitzer Strasse, Jena, Germany). Color coding was performed using the IMT i-solution software (IMT i-solution Inc., Vancouver, BC, Canada). To determine the levels of Aβ aggregation among GFP positive cells, the number of Aβ positive cells vs. GFP positive cells was counted in 20 random fields per culture. For confocal microscopy analysis, is fluorescence signals were visualized using a confocal microscope (TCS SP2, LEICA, Ernst-Leitz-Strasse, Wetzlar, Germany).

Subcellular Fractionation

To determine the intracellular localization of the NIa protein, NIa-expressing cells were fractionated using protocol previously described[53]. Briefly, the cells were harvested by scraping into homogenation buffer (200 mM sucrose, 20 mM Tris [pH7.4], 1 mM EGTA, 1 mM EDTA, 1× complete protease inhibitor cocktail), lysed by multiple passages through a syringe with a 26-gauge needle, and ultracentrifuged at 70,000×g for 30 min at 4° C. The pellet (crude membrane fraction) was resuspended in homogenation buffer containing 0.5% Triton X-100 and sonicated for 1 min. Aliquots (50 µg) from each fraction were analyzed by Western blotting.

Electrophoresis and Western Blotting

The cells were harvested after washing three times with PBS, resuspended in RIPA buffer containing 1× protease inhibitor cocktail and sonicated briefly. The soluble protein fraction was recovered after centrifugation at 10,000×g for 30 min and separated by SDS-PAGE. Protein concentration was determined by the BCA method. For the analysis of Aβ peptides, samples were separated by electrophoresis using 10-20% Tris-Tricine gels. Proteins were then transferred onto PVDF membrane in 50 mM Tris, 192 mM glycine, and 20% methanol. Membranes were blocked with 5% non-fat milk and incubated with antibodies against 6E10, HA, α-tubulin, VDAC2, Oct1, and cathepsin D. Bands were visualized using the ECL reagent (GE Healthcare/Amersham Bioscience, Piscataway, N.J., USA) and the intensity of each band was quantified by densitometry (Bio-Rad).

Production of Lentiviruses

The cDNA fragments encoding NIa and GFP were subcloned into the pLEX-MCS lentiviral vector (Openbiosystems, Huntsville, Ala., USA). The resulting recombinant plasmids were co-transformed with packing plasmids into 293T cells and the supernatants were collected. Lentiviruses were collected and concentrated by ultra-centrifugation as previously described[19,54]. The titers of the NIa and GFP lentiviruses were estimated by measuring the amount of HIV p24 antigen using PCR.

AD Murine Model and Surgical Procedure

Transgenic AD model mice, Tg-APPswe/PS1dE9, overexpressing human mutated APP and PS1 (APPswe/PS1dE9), were maintained in C57BL6×C3H F1 hybrid mice, as described previously[55]. The mice were housed in normal plastic cages with free access to food and water in a temperature- and humidity-controlled environment under a 12 h light/dark cycle (lights on at 7 a.m.), and they were fed a diet of lab chow and water ad libitum. Tg-APPswe/PS1dE9 mice at 6.5 months of age were randomized into the Lenti-NIa (n=9) and Lenti-GFP (n=10) groups. The mice underwent bilateral intracerebroventricular (i.c.v.) infusion with 3 µl of Lenti-NIa lentivirus (1×108 TU) or Lenti-GFP lentivirus with the same titer. After one month, the injected mice were sacrificed and perfused with 0.9% saline. The right and left hemispheres of the brain were used for histological and biochemical analyses, respectively. All animals were handled in accordance with the animal care guidelines of the Ewha Womans University School of Medicine.

RT-PCR

Total RNA was isolated with TRI reagent (Sigma) from frontal cerebral cortex tissue. Reverse-transcription was performed using ImProm II reverse-transcriptase is (Promega, Madison, Wis., USA) with oligo-dT priming. To detect NIa expression, PCR was performed using the NIa specific primer set: 5'-ACG AAA GAC GGC CAA TGC GGA-3' and 5'-ACC CGA CGG TTG CGA TGC TT-3'. And for control experiment, PCR was performed using the GAPDH specific primer set: 5'-TCC GTG TTC CTA CCC CCA ATG-3' and 5'-GGG AGT TGC TGT TGA AGT CGC-3'.

Immunohistochemistry

The right hemisphere was post-fixed with 4% paraformaldehyde in 0.1 M phosphate buffer (pH 7.4) at 4° C. overnight and were coronally cut into 40 µm-thick sections with a vibratome (Leica VT 1000S; Leica, Germany). Free-floating sections were blocked by 5% normal goat serum, 2% BSA, and 2% FBS. A biotinylated HRP system was used for color development. Anti-Aβ antibody Bam-10 (A5213) was purchased from Sigma (USA). Microscopic studies were carried out using an Oympus BX 51 microscope equipped with a DP71 camera and DP-B software (Olympus, Japan). For the quantification of plaque levels, the numbers of plaques in each region were measured using the TOMORO ScopeEye 3.6 program (Techsan Community, Seoul, Korea).

Assessment of Aβ Levels

ELISA assays for Aβ(1-42) and Aβ(1-40) levels were described in a previous study[46]. Briefly, the frontal cerebral cortex was homogenized in Tris-buffered saline (20 mM Tris and 137 mM NaCl, [pH 7.6]) in the presence of protease inhibitor mixtures (Complete Mini; Roche, USA). Homogenates were centrifuged at 100,000×g for 1 hr at 4° C., and the supernatant was used to measure the levels of Tris buffer-soluble forms of Aβ. The pellet was sonicated in 70% formic acid and centrifuged as above; the resulting supernatant was considered the formic acid extractable Aβ and collected for further analysis. The formic acid extract was neutralized with 1 M Tris-Cl buffer (pH 11) in a dilution ratio of 1:20 before its use as previously described. The final assays were performed using Human Aβ(1-40) or Aβ(1-42) colorimetric sandwich ELISA kits (BioSource, Invitrogen) by following the manufacturer's instructions.

Statistical Analysis

Two sample-comparisons were carried out using the unpaired Student's t test with unequal variance, while multiple comparisons were made by one-way ANOVA followed by the Newman-Keuls multiple range test. A p value of less than 0.05 was accepted as being statistically significant. Data are presented as mean±SD.

Results

Cleavage of Monomeric and Oligomeric Aβ by NIa

Figure 1B:
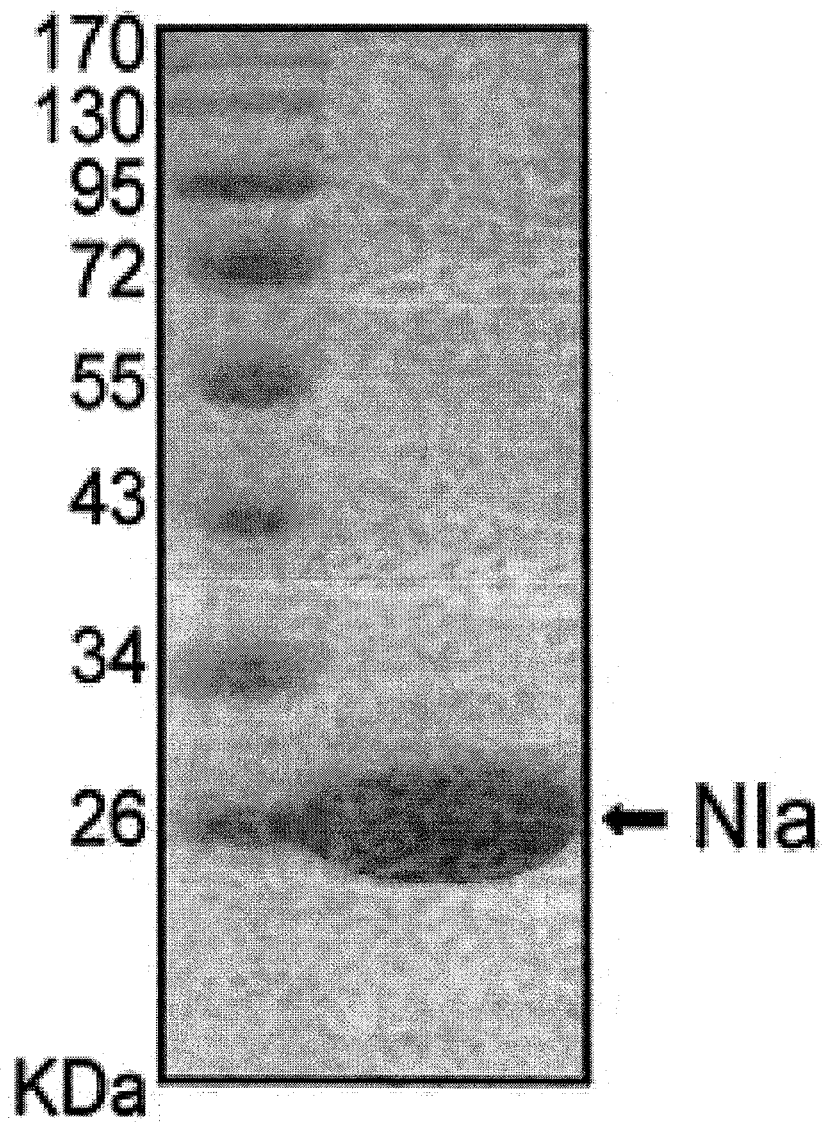
Figure 1C:
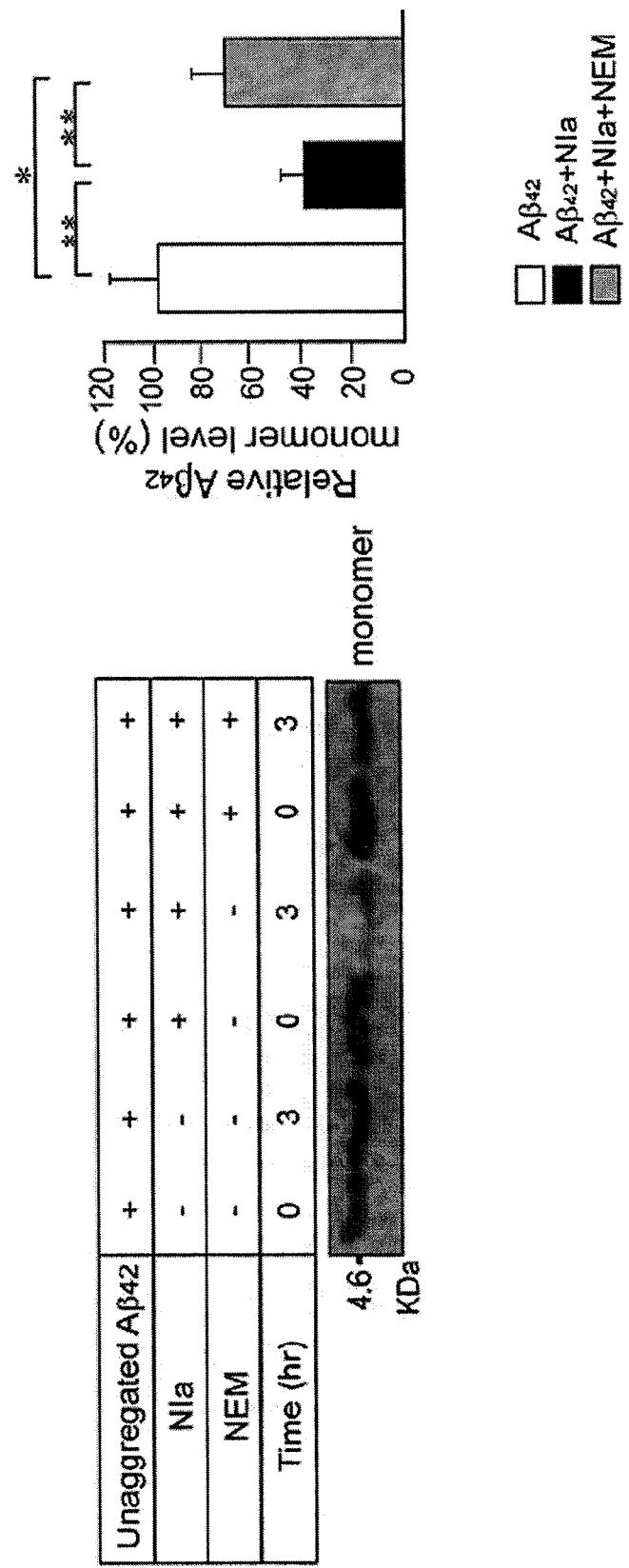

We have previously reported that NIa possesses a highly strict substrate specificity, with its cleavage sites defined by the conserved sequence motif Val-Xaa-His-Gln↓, in which the scissile bond is located after Gln. Interestingly, the sequence Val-His-His-Gln is present in Aβ in the vicinity of the presumed α-secretase cleavage site (FIG. 1A). Based on this finding, we aimed to determine whether NIa can specifically cleave A. For this purpose, a recombinant NIa protein was expressed in *E. coli* and purified to homogeneity on a chitin bead column (FIG. 1B). NIa was then incubated with a monomeric Aβ preparation for 3 hrs in the presence or absence of the cysteine protease inhibitor, NEM. Analysis by Western blotting revealed that the monomeric Aβ level was greatly reduced by NIa (FIG. 1C, lane 2 vs. 4), which was partially reversed in the presence of NEM (FIG. 1C, lane 6). The results of the densitometry analysis showed that NIa reduced Aβ levels by 64% in the absence of NEM and 33% in the presence of NEM, suggesting the specific cleavage of monomeric Aβ by NIa.

Figure 1D:
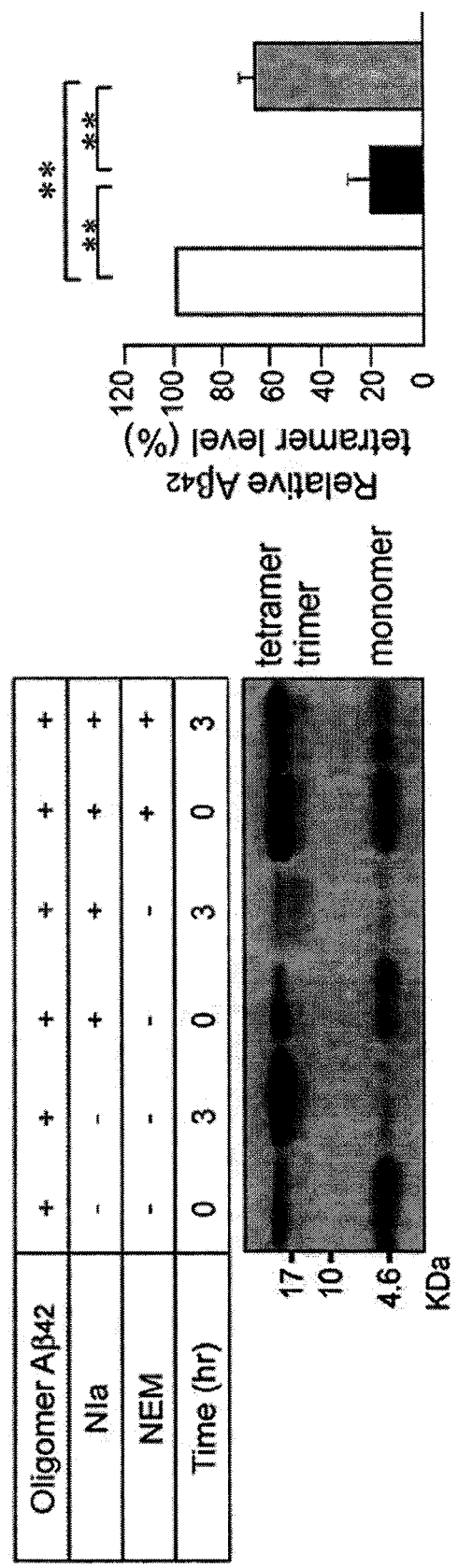

Our findings show that NEM did not completely inhibit NIa activity, which is consistent with a previous report showing that mutations of cysteine residues in the catalytic triad of NIa did not completely abolish its proteolytic activity[23]. We then tested whether NIa is capable of cleaving oligomeric Aβ, which is known to be more toxic than monomeric Aβ. Oligomeric Aβ was prepared by incubating a solution of Aβ peptides at 4° C. for 36 hrs. As assessed by SDS-PAGE, the oligomeric Aβ preparation contained roughly equal amounts of monomeric and oligomeric Aβ (FIG. 1D, lanes 1, 3, and 5), a balance that shifted toward an increase in the formation of oligomeric Aβ at the expense of monomeric Aβ after an additional 3 hour incubation at 25°

C. Our findings are consistent with a previous report showing that Aβ oligomerization was accelerated by an increase in incubation time and temperature[24]. Under the same conditions, the amount of oligomeric Aβ was greatly reduced by NIa (lane 4) as quantified by densitomeric assessment, which showed that only 19% of oligomeric Aβ remained. This NIa-mediated reduction of oligomeric Aβ was significantly blocked by NEM (lane 6) implying that NIa specifically cleaves Aβ.

To further analyze the specific cleavage of Aβ by NIa, the cleavage products were analyzed by MALDI-TOF/TOF mass spectrometry (FIG. 2). The monomeric Aβ preparation produced a single peak without contamination, whereas NIa produced three contaminating peaks. In the reaction mixture including Aβ and NIa, the peak corresponding to Aβ was greatly reduced and two new peaks were detected (FIG. 2B), with molecular weights of 1,826 Da and 2,704 Da, corresponding to amino acids 1-15 and 16-42 of Aβ, respectively (FIG. 2A). This result indicates that NIa cleaves the peptide bond after Gln[15], as expected.

Subcellular Localization of NIa

B103 neuroblastoma cells were transformed with an HA-tagged NIa expression vector and stained with an anti-HA antibody. Examination with confocal microscopy revealed that NIa was expressed predominantly in the cytoplasm (FIG. 3A). The transformed cells were fractionated into the particulate (P) and soluble (S) fractions and subjected to Western blotting (FIG. 3B). While Oct1 (nuclear marker), VDAC2 (mitochondrial marker), and cathepsin D (lysosomal marker) were found in the particulate fraction, HA was colocalized with α-tubulin (cytosolic marker) exclusively to the soluble fraction. These data suggest that NIa resides predominantly in the cytosol.

NIa Prevents Aβ-Induced Cell Death

To test whether NIa possesses activity against A within cells, we generated Aβ intracellularly using the plasmid pGFPUb-A, encoding a triple fusion protein of green fluorescent protein (GFP), ubiquitin (Ub), and Aβ. The peptide bond between Ub and Aβ is cleaved quickly by endogenous deubiquitinating enzymes, generating an equimolar ratio of GFP-Ub and Aβ in the cytosol[52]. B103 cells were co-transformed with pGFPUb-Aβ and an empty plasmid, a NIa-expression plasmid, pcDNA-HA-NIa, or a mutant NIa expression plasmid, pcDNA-HA-mNIa. The NIa mutation consisted of an Asp to Ala substitution in the catalytic triad. The cells were then immunostained with the anti-Aβ antibody, 6E10 (FIGS. 4A and B). The results revealed that the proportion of Aβ-positive cells was 56% of the total of GFP-positive cells in those cells harboring pGFPUb-Aβ and an empty plasmid (Mock), whereas the ratio sharply declined to 14% in cells harboring pGFPUb-Aβ and pcDNA-HA-NIa (NIa). The observed ratio in those cells expressing a mutant NIa protease plasmid (mNIa) was 42%, which was not significantly different from that obtained with an empty plasmid. These data indicate that NIa can specifically degrade intracellular Aβ.

To evaluate whether NIa prevents Aβ-induced cell death, we used two different methods, a morphological approach and the MTT cell viability assay (FIGS. 4B and C). Intracellular expression of Aβ via pGFPUb-Aβ resulted in a significant increase in cell death (62% by the morphological assay and 55% by the MTT assay). This intracellular Aβ-induced cell death was almost completely blocked by co-transfomation with pcDNA-HA-NIa but it was not affected in cells co-expressing pcDNA-HA-mNIa. Treatment of B103 cells with exogenous Aβ also resulted in a considerable proportion of cell death (40% by the morphological assay and 38% by the MTT assay), which was inhibited by co-transfomation with pcDNA-HA-NIa but not by pcDNA-HA-mNIa co-expression (FIGS. 5A and B). It was previously shown that extracellular Aβ is internalized by cell surface receptors and detected in subcellular organelles such as lysosomes, mitochondria and cytosol, causing cell death through dysfunction of these organelles[56-59]. It appears that cytosolic NIa can cleave internalized Aβ, although it is unknown whether NIa and internalized Aβ are co-localized. Nonetheless, our data indicate that NIa can prevent cell death induced by both intracellularly expressed and exogenously added Aβ.

Lentiviral-Mediated Overexpression of NIa

Figure 6A:
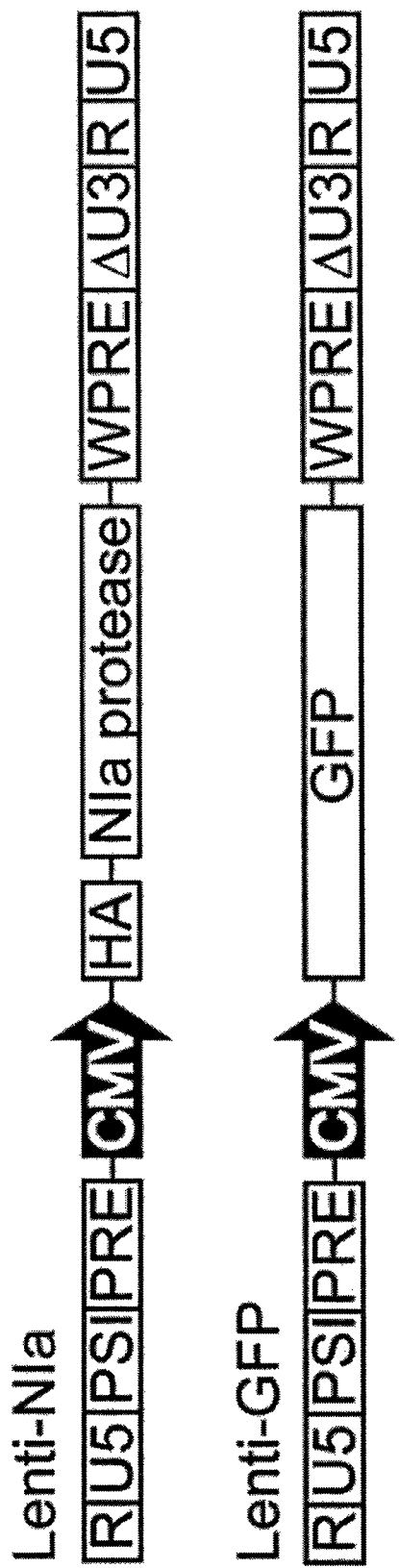
Figure 6B:
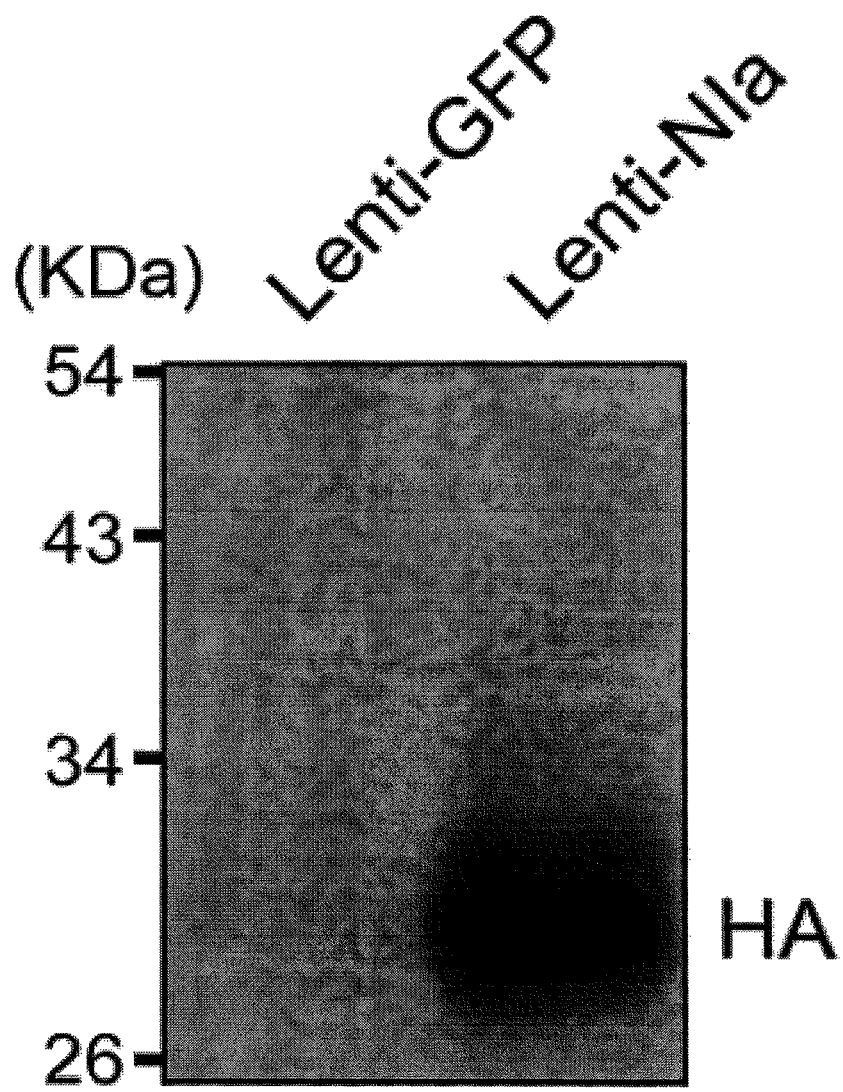
Figure 6C:
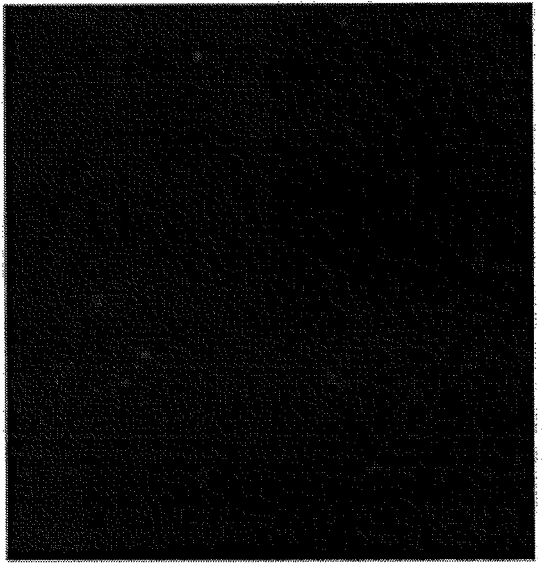
Figure 6C:
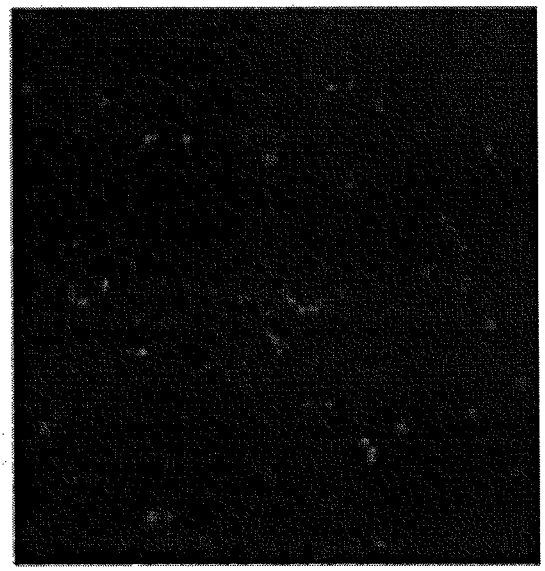
Figure 6D:
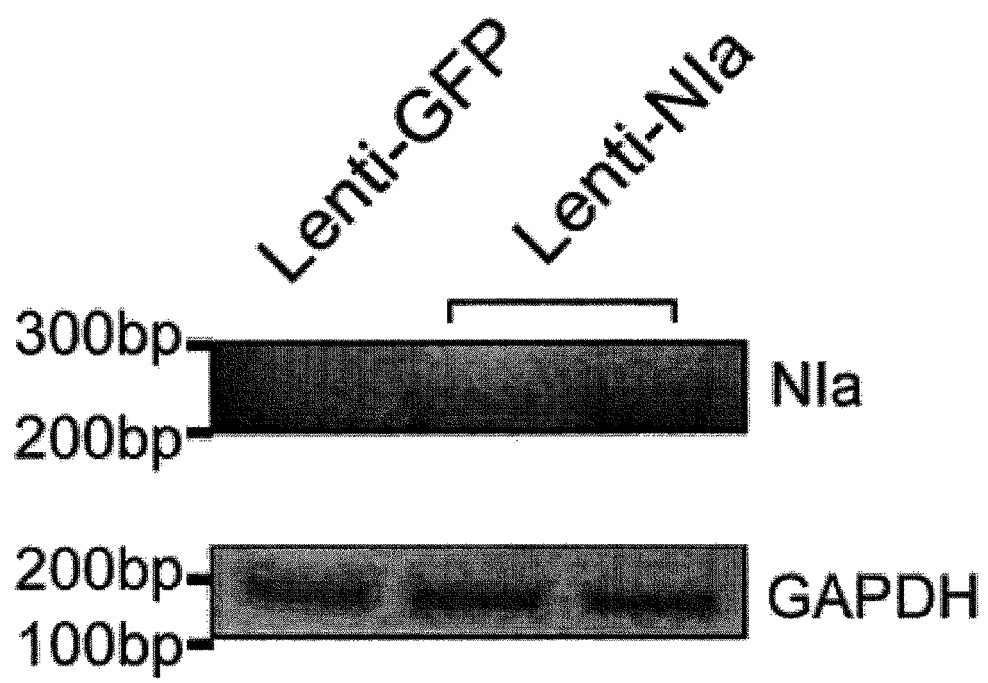

Lentiviral vectors expressing NIa and GFP were generated (FIG. 6A). Human 293T cells infected with Lenti-NIa showed a strong NIa expression, as assessed by Western blotting with anti-HA antibody (FIG. 6B). Double transgenic mice (APPswe/PS1dE9) were stereotaxically injected with 3 μl of Lenti-NIa (1×108 TU) into the lateral ventricles. To evaluate the expression of NIa, immunohistochemistry was performed one month after injection. The NIa expression was detected in sections of mice injected with Lenti-NIa compared with the brain sections of control non-injected mice (FIG. 6C). The pattern of NIa expression showed a wide distribution throughout the brain including the cerebral cortex, hippocampus, amygdala, and thalamus (data not shown). RT-PCR also showed the presence of the NIa transcripts in the Lenti-NIa-infected brain. The GAPDH signal served as a control and was equally expressed in all samples (FIG. 6D).

Decreased Aβ Levels in the Brain of APPsw/PS1 Transgenic Mice Infused with Lenti-NIa To assess if NIa causes a reduction in the Aβ levels in mouse brains, Lenti-NIa was infused into the lateral ventricles of the brain of APPsw/PS1dE9 mice at 6.5 months of age. As a control, equal amounts of Lenti-GFP were infused in the same manner. The brains were removed one month after injection and the A levels in both soluble (Tris-buffer extractable) and insoluble (FA-buffer extractable) fractions were measured by ELISA. We found that the levels of both $A\beta_{1-40}$ and $A\beta_{1-42}$ were significantly reduced in both the soluble and insoluble factions of Lenti-NIa-infused brain when compared to the Lenti-GFP-infused brain (FIG. 7A). The Lenti-NIa infusion reduced the soluble $A\beta_{1-40}$ by 33% in males and by 36% in females, and the insoluble $A\beta_{1-40}$ by 24% in males and by 21% in females (FIG. 7A, upper lane). NIa also reduced the soluble $A\beta_{1-42}$ by 38% in males and by 28% in females, and the insoluble $A\beta_{1-42}$ by 33% in males and by 36% in females (FIG. 7A, lower lane). The reduction of $A\beta_{1-42}$ levels in the male brains was not statistically significant.

Reduced Aβ Deposition in the Brain of $APP_{sw}$/PS1 Transgenic Mice Infused with Lenti-NIa Immunohistochemical analysis revealed that the A deposition in the prefrontal cortex, parietal cortex, hippocampus and piriform cortex was remarkably decreased in the brain infused with Lenti-NIa in comparison to the brain infused with Lenti-GFP (FIG. 7B). Quantitative assessment of Aβ levels indicated that the Lenti-NIa infusion reduced the plaques by 58% in the prefrontal cortex, by 62% in the parietal cortex, and by 59% in the piriform cortex (FIG. 7C).

Discussion

The generation and accumulation of Aβ is the most critical event in the development of AD, suggesting that the clearance of Aβ could provide a valuable strategy for the treatment of AD. Although Aβ exits in several assembly and aggregation forms, oligomeric Aβ is known to be the most toxic form. Aβ is oligomerized intracellularly soon after it is generated, and these molecules are then secreted from the cell. Some of the secreted Aβ oligomers enter the cell through selective uptake and subsequently cause the dysfunction of subcellular organelles, which is associated with the memory and cognitive decline typically observed in AD patients[60].

Aβ is detected in both intraneuronal cells and in the extracellular space of AD brains. Recent studies have demonstrated that intracellular Aβ levels decrease as extracellular plaques start to build up in patients with AD and in AD transgenic mouse models[10,61]. These results suggest that the accumulation of intracellular Aβ precedes the formation of extracellular Aβ deposits in the progression of the disease. Interestingly, in cells expressing the AD-associated mutant APP, Aβ is kept within the cells, whereas in cells expressing wild type APP, Aβ is mostly found to be secreted[32]. In addition, in aged mice carrying mutant presenilin 1, Aβ aggregation is detected within neurons, but it is absent in the extracellular fluid[62]. The inhibition of proteasome activity leads to higher levels of Aβ both in vivo and in vitro, suggesting that the proteasome is responsible for the processing of Aβ in the cytosol[52,63,64]. The overproduction of Aβ results in an overload of the proteasome, ultimately leading to an impairment of proteasome activity, a characteristic of AD[65,66].

These reports support a central role for intracellular Aβ in the pathogenesis of AD. The enhanced proteosomal activity caused by the plant polyphenol resveratrol was shown to reduce intracellular as well as extracellular Aβ levels and to prevent neurodegenerative disorders[67]. Parkin is an E3 ligase which participates in the ubiquitination of intracellularly expressed Aβ. The overexpression of parkin was found to result in a proteasome-mediated reduction of Aβ levels[68], whereas the knockout of parkin caused an accumulation of Aβ deposits[68,69]. Enhanced clearance of intracellular Aβ may therefore prevent plaque formation, secondary pathology and premature death.

In this study, we show that a plant viral protease, NIa, specifically cleaves oligomeric as well as monomeric Aft in vitro and is predominantly localized in the cytosol of neuronal cells.

The expression of NIa in neuronal cells inhibits cell death induced both by intracellularly expressed and exogenously added Aβ. In addition, lentiviral-mediated overexpression of NIa in the brain of AD transgenic mice was found to reduce the levels of Aβ and plaque formation. These data provide additional evidence supporting a critical role for intracellular Aβ in the pathogenesis of AD. In this regard, NIa could be used as a novel tool to study the molecular events underlying the induction of cell death by intracellular Aβ. Finally, our results offer proof-of-concept that the clearance of intracellular Aβ by a cytosolic protease could be a viable strategy for the treatment of AD.

Acknowledgements

This work was supported by the National Research Foundation of Korea (NRF) grant funded by the Korea government (MEST) (No. 2009-0085747) and by the Systems Biology Infrastructure Establishment Grant provided by Gwangju Institute of Science & Technology.

REFERENCES

1 LaFerla F M, Green K N, Oddo S. Intracellular amyloid-beta in Alzheimer's disease. *Nat Rev Neurosci* 2007; 8: 499-509.
2 Blennow K, de Leon M J, Zetterberg H. Alzheimer's disease. *Lancet* 2006; 368: 387-403.
3 Dahlgren K N et al. Oligomeric and fibrillar species of amyloid-beta peptides differentially affect neuronal viability. *J Biol Chem* 2002; 277: 32046-32053.
4 Ono K, Condron M M, Teplow D B. Structure-neurotoxicity relationships of amyloid beta-protein oligomers. *Proc Natl Acad Sci USA* 2009; 106: 14745-14750.
5 Masters C L et al. Amyloid plaque core protein in Alzheimer disease and Down syndrome. *Proc Natl Acad Sci USA* 1985; 82: 4245-4249.
6 Pike C J et al. Neurodegeneration induced by beta-amyloid peptides in vitro: the role of peptide assembly state. *J Neurosci* 1993; 13: 1676-1687.
7 Wirths O, Multhaup G, Bayer T A. A modified beta-amyloid hypothesis: intraneuronal accumulation of the beta-amyloid peptide—the first step of a fatal cascade. *J Neurochem* 2004; 91: 513-520.
8 Mod C et al. Intraneuronal Abeta42 accumulation in Down syndrome brain. *Amyloid* 2002; 9: 88-102.
9 Grant S M, Ducatenzeiler A, Szyf M, Cuello A C. Abeta immunoreactive material is present in several intracellular compartments in transfected, neuronally differentiated, P19 cells expressing the human amyloid beta-protein precursor. *Alzhekimers Dis* 2000; 2: 207-222.
10 Billings L M et al. Intraneuronal Abeta causes the onset of early Alzheimer's disease-related cognitive deficits in transgenic mice. *Neuron* 2005; 45: 675-688.
11 Zhang Y, McLaughlin R, Goodyer C, LeBlanc A. Selective cytotoxicity of intracellular amyloid beta peptidel-42 through p53 and Bax in cultured primary human neurons. *J Cell Biol* 2002; 156: 519-529.
12 Ohyagi Y et al. Intracellular Abeta42 activates p53 promoter: a pathway to neurodegeneration in Alzheimer's disease. *Faseb J* 2005; 19: 255-257.
13 Wang X et al. Insights into amyloid-beta-induced mitochondrial dysfunction in Alzheimer disease. *Free Radic Biol Med* 2007; 43: 1569-1573.
14 Oddo S et al. Abeta immunotherapy leads to clearance of early, but not late, hyperphosphorylated tau aggregates via the proteasome. *Neuron* 2004; 43: 321-332.
15 Oddo S et al. A dynamic relationship between intracellular and extracellular pools of Abeta. *Am J Pathol* 2006; 168: 184-194.
16 Selkoe D J. Clearing the brain's amyloid cobwebs. *Neuron* 2001; 32: 177-180.
17 Mouri A et al. Inhibition of neprilysin by thiorphan (i.c.v.) causes an accumulation of amyloid beta and impairment of learning and memory. *Behav Brain Res* 2006; 168: 83-91.
18 Farris W et al. Loss of neprilysin function promotes amyloid plaque formation and causes cerebral amyloid angiopathy. *Am J Pathol* 2007; 171: 241-251.
19 Marr R A et al. Neprilysin gene transfer reduces human amyloid pathology in transgenic mice. *J Neurosci* 2003; 23: 1992-1996.
20 Leissring M A et al. Enhanced proteolysis of beta-amyloid in APP transgenic mice prevents plaque formation, secondary pathology, and premature death. *Neuron* 2003; 40: 1087-1093.
21 Meilandt W J et al. Neprilysin overexpression inhibits plaque formation but fails to reduce pathogenic Abeta oligomers and associated cognitive deficits in human amyloid precursor protein transgenic mice. *J Neurosci* 2009; 29: 1977-1986.
22 Lockett L J, Molloy P L, Russell P J, Both G W. Relative efficiency of tumor cell killing in vitro by two enzyme- 23 Wang G et al. Feline immunodeficiency virus vectors persistently transduce nondividing airway epithelia and correct the cystic fibrosis defect. *J Clin Invest* 1999; 104: R55-62.

24 Chambers R et al. Comparison of genetically engineered herpes simplex viruses for the treatment of brain tumors in a scid mouse model of human malignant glioma. *Proc Natl Acad Sci USA* 1995; 92: 1411-1415.

25 Puhlmann M et al. Thymidine kinase-deleted vaccinia virus expressing purine nucleoside phosphorylase as a vector for tumor-directed gene therapy. Hum *Gene Ther* 1999; 10: 649-657.

26 Riordan J R et al. Identification of the cystic fibrosis gene: cloning and characterization of complementary DNA. *Science* 1989; 245: 1066-1073.

27 Ghosh-Choudhury G, Haj-Ahmad Y, Graham F L. Protein IX, a minor component of the human adenovirus capsid, is essential for the packaging of full length genomes. *Embo J* 1987; 6: 1733-1739.

28 Mann R, Mulligan R C, Baltimore D. Construction of a retrovirus packaging mutant and its use to produce helper-free defective retrovirus. *Cell* 1983; 33: 153-159.

29 Ridgway A A. Mammalian expression vectors. *Biotechnology* 1988; 10: 467-492.

30 Kasahara N, Dozy A M, Kan Y W. Tissue-specific targeting of retroviral vectors through ligand-receptor interactions. *Science* 1994; 266: 1373-1376.

31 LaFace D, Hermonat P, Wakeland E, Peck A. Gene transfer into hematopoietic progenitor cells mediated by an adeno-associated virus vector. *Virology* 1988; 162: 483-486.

32 Zhou S Z et al. Adeno-associated virus 2-mediated gene transfer in murine hematopoietic progenitor cells. *Exp Hematol* 1993; 21: 928-933.

33 Walsh C E et al. Phenotypic correction of Fanconi anemia in human hematopoietic cells with a recombinant adeno-associated virus vector. *J Clin Invest* 1994; 94: 1440-1448.

34 Flotte T R et al. An improved system for packaging recombinant adeno-associated virus vectors capable of in vivo transduction. *Gene Ther* 1995; 2: 29-37.

35 McLaughlin S K, Collis P, Hermonat P L, Muzyczka N. Adeno-associated virus general transduction vectors: analysis of proviral structures. *J Virol* 1988; 62: 1963-1973.

36 Samulski R J, Chang L S, Shenk T. Helper-free stocks of recombinant adeno-associated viruses: normal integration does not require viral gene expression. *J Virol* 1989; 63: 3822-3828.

37 McCarty D M, Christensen M, Muzyczka N. Sequences required for coordinate induction of adeno-associated virus p19 and p40 promoters by Rep protein. *J Virol* 1991; 65: 2936-2945.

38 Coupar B E, Andrew M E, Boyle D B. A general method for the construction of recombinant vaccinia viruses expressing multiple foreign genes. *Gene* 1988; 68: 1-10.

39 Nicolau C, Sene C. Liposome-mediated DNA transfer in eukaryotic cells. Dependence of the transfer efficiency upon the type of liposomes used and the host cell cycle stage. *BiochiM Biophys Acta* 1982; 721: 185-190.

40 Nicolau C, Legrand A, Grosse E. Liposomes as carriers for in vivo gene transfer and expression. Methods Enzymol 1987; 149: 157-176.

41 Capecchi M R. High efficiency transformation by direct microinjection of DNA into cultured mammalian cells. *Cell* 1980; 22: 479-488.

42 Harland R, Weintraub H. Translation of mRNA injected into *Xenopus* oocytes is specifically inhibited by antisense RNA. *J Cell Biol* 1985; 101: 1094-1099.

43 Graham F L, van der Eb A J. A new technique for the assay of infectivity of human adenovirus 5 DNA. *Virology* 1973; 52: 456-467.

44 Chen C, Okayama H. High-efficiency transformation of mammalian cells by plasmid DNA. *Mol Cell Biol* 1987; 7: 2745-2752.

45 Neumann E, Schaefer-Ridder M, Wang Y, Hofschneider P H. Gene transfer into mouse lyoma cells by electroporation in high electric fields. *Embo J* 1982; 1: 841-845.

46 Tur-Kaspa R et al., Use of electroporation to introduce biologically active foreign genes into primary rat hepatocytes. *Mol Cell Biol* 1986; 6: 716-718.

47 Wong T K, Nicolau C, Hofschneider P H. Appearance of beta-lactamase activity in animal cells upon liposome-mediated gene transfer. *Gene* 1980; 10: 87-94.

48 Gopal T V. Gene transfer method for transient gene expression, stable transformation, and cotransformation of suspension cell cultures. *Mol Cell Biol* 1985; 5: 1188-1190.

49 Yang N S et al. In vivo and in vitro gene transfer to mammalian somatic cells by particle bombardment. *Proc Natl Acad Sci USA* 1990; 87: 9568-9572.

50 Yan P et al. Matrix metalloproteinase-9 degrades amyloid-beta fibrils in vitro and compact plaques in situ. *J Biol Chem* 2006; 281: 24566-24574.

51 Song S et al. E2-25K/Hip-2 regulates caspase-12 in ER stress-mediated Abeta neurotoxicity. *J Cell Biol* 2008; 182: 675-684.

52 Lee E K et al. Cytosolic amyloid-beta peptide 42 escaping from degradation induces cell death. *Biochem Biophys Res Commun* 2006; 344: 471-477.

53 Lehel C et al. Overexpressed protein kinase C-delta and -epsilon subtypes in NIH 3T3 cells exhibit differential subcellular localization and differential regulation of sodium-dependent phosphate uptake. *J Biol Chem* 1994; 269: 4761-4766.

54 Dull T et al. A third-generation lentivirus vector with a conditional packaging system. *J Virol* 1998; 72: 8463-8471.

55 Jankowsky J L et al. Co-expression of multiple transgenes in mouse CNS: a comparison of strategies. *Biomol Eng* 2001; 17: 157-165.

56 Hansson Petersen C A et al. The amyloid beta-peptide is imported into mitochondria via the TOM import machinery and localized to mitochondrial cristae. *Proc Natl Acad Sci USA* 2008; 105: 13145-13150.

57 Chafekar S M, Baas F, Scheper W. Oligomer-specific Abeta toxicity in cell models is mediated by selective uptake. *Biochim Biophys Acta* 2008; 1782: 523-531.

58 Almeida C G, Takahashi R H, Gouras G K. Beta-amyloid accumulation impairs multivesicular body sorting by inhibiting the ubiquitin-proteasome system. *J Neurosci* 2006; 26: 4277-4288.

59 Takuma K et al. RAGE-mediated signaling contributes to intraneuronal transport of amyloid-beta and neuronal dysfunction. *Proc Natl Acad Sci USA* 2009; 106: 20021-20026.

60 Walsh D M et al. Naturally secreted oligomers of amyloid beta protein potently inhibit hippocampal long-term potentiation in vivo. *Nature* 2002; 416: 535-539.

61 Gyure K A et al. Intraneuronal abeta-amyloid precedes development of amyloid plaques in Down syndrome. *Arch Pathol Lab Med* 2001; 125: 489-492.
62 Chui D H et al. Transgenic mice with Alzheimer presenilin 1 mutations show accelerated neurodegeneration without amyloid plaque formation. *Nat Med* 1999; 5: 560-564.
63 Song S, Jung Y K. Alzheimer's disease meets the ubiquitin-proteasome system. *Trends Mol Med* 2004; 10: 565-570.
64 Oddo S. The ubiquitin-proteasome system in Alzheimer's disease. *J Cell Mol Med* 2008; 12: 363-373.
65 Gregori L et al. Amyloid beta-protein inhibits ubiquitin-dependent protein degradation in vitro. *J Biol Chem* 1995; 270: 19702-19708.
66 Keller J N, Hanni K B, Markesbery W R. Impaired proteasome function in Alzheimer's disease. *J Neurochem* 2000; 75: 436-439.
67 Marambaud P, Zhao H, Davies P. Resveratrol promotes clearance of Alzheimer's disease amyloid-beta peptides. *J Biol Chem* 2005; 280: 37377-37382.
68 Burns M P et al. Parkin promotes intracellular Abeta1-42 clearance. *Hum Mol Genet.* 2009; 18: 3206-3216.
69 Rodriguez-Navarro J A et al. Parkin deletion causes cerebral and systemic amyloidosis in human mutated tau over-expressing mice. *Hum Mol Genet.* 2008; 17: 3128-3143.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for treating an amyloid β-caused disease, which comprises administering to a mammalian subject a pharmaceutical composition comprising as an active ingredient an isolated or synthesized nuclear inclusion a NIa protease of Turnip mosaic virus (TuMV) consisting of the amino acid sequence of SEQ ID NO:1 or a gene carrier containing a nucleotide sequence encoding the NIa protease of TuMV, wherein the gene carrier is (i) a naked recombinant DNA molecule, (ii) a plasmid, (iii) a viral vector selected from the group consisting of adenovirus, adeno-associated virus, retrovirus, lentivirus, herpes simplex virus and vaccinia virus, or (iv) a liposome or a niosome containing a naked recombinant DNA molecule and a plasmid; and wherein the NIa protease cleaves intracellular or extracellular amyloid β.

2. The method according to claim 1, wherein the NIa protease cleaves amyloid β present in cytosol.

3. The method according to claim 1, wherein the NIa protease inhibits the amyloid β-induced cell death.

4. The method according to claim 1, wherein the NIa protease has the activity to cleave an oligomeric amyloid β.

5. The method according to claim 1, wherein the NIa protease has the activity to cleave amyloid $β_{1-40}$ and amyloid $β_{1-42}$.

6. The method according to claim 1, wherein the NIa protease has the activity to cleave a peptide bond between amino acids 15 and 16 of SEQ ID NO:3.

7. The method according to claim 1, wherein the gene carrier is a viral vector and the viral vector is a lentiviral vector.

8. The method according to claim 1, wherein the amyloid β-caused disease is a disease selected from the group consisting of Alzheimer's disease, MCI (mild cognitive impairment), mild-to-moderate cognitive impairment, vascular dementia, cerebral amyloid angiopathy, hereditary cerebral hemorrhage, senile dementia, Down's syndrome, inclusion body myositis, age-related macular degeneration and conditions associated with Alzheimer's disease.

9. The method according to claim 8, wherein the amyloid β-caused disease is Alzheimer's disease.

* * * * *